US012584905B2

(12) United States Patent
Msika et al.

(10) Patent No.: US 12,584,905 B2
(45) Date of Patent: Mar. 24, 2026

(54) METHOD FOR IDENTIFYING MOLECULAR MARKERS OF CHILDREN'S SKIN

(71) Applicant: LABORATOIRES EXPANSCIENCE, Courbevoie (FR)

(72) Inventors: Philippe Msika, Versailles (FR); Caroline Baudouin, Rambouillet (FR)

(73) Assignee: Laboratoires Expanscience, Paris la Defense (FR)

( * ) Notice: Subject to any disclaimer, the term of this patent is extended or adjusted under 35 U.S.C. 154(b) by 1326 days.

(21) Appl. No.: 14/414,253

(22) PCT Filed: Jul. 15, 2013

(86) PCT No.: PCT/EP2013/064926
§ 371 (c)(1),
(2) Date: Jun. 29, 2015

(87) PCT Pub. No.: WO2014/009566
PCT Pub. Date: Jan. 16, 2014

(65) Prior Publication Data
US 2015/0285787 A1 Oct. 8, 2015

(30) Foreign Application Priority Data
Jul. 13, 2012 (FR) ...................................... 1256766

(51) Int. Cl.
| | |
|---|---|
| *C12Q 1/68* | (2018.01) |
| *C12Q 1/6876* | (2018.01) |
| *C12Q 1/6888* | (2018.01) |
| *G01N 33/50* | (2006.01) |
| *G01N 33/68* | (2006.01) |
| *G01N 33/92* | (2006.01) |

(52) U.S. Cl.
CPC ....... *G01N 33/5044* (2013.01); *C12Q 1/6876* (2013.01); *C12Q 1/6888* (2013.01); *G01N 33/5088* (2013.01); *G01N 33/6881* (2013.01); *G01N 33/6893* (2013.01); *G01N 33/92* (2013.01); *C12Q 2600/148* (2013.01); *C12Q 2600/158* (2013.01); *G01N 2800/20* (2013.01); *G01N 2800/60* (2013.01)

(58) Field of Classification Search
None
See application file for complete search history.

(56) References Cited

U.S. PATENT DOCUMENTS

| | | | |
|---|---|---|---|
| 4,849,077 A | 7/1989 | Rosenthal et al. | |
| 4,882,127 A | 11/1989 | Rosenthal et al. | |
| 6,723,513 B2 | 4/2004 | Lexow | |
| 7,556,922 B2 | 7/2009 | Block et al. | |
| 9,089,576 B2 * | 7/2015 | Piccirilli ................. | A61P 17/02 |
| 2003/0068663 A1 | 4/2003 | Huang et al. | |
| 2006/0275782 A1 | 12/2006 | Gunderson et al. | |

| | | | |
|---|---|---|---|
| 2007/0148771 A1 | 6/2007 | Chopart et al. | |
| 2008/0020392 A1 | 1/2008 | Block et al. | |
| 2009/0181385 A1 | 7/2009 | Mckernan et al. | |
| 2009/0181860 A1 | 7/2009 | Mckernan et al. | |
| 2009/0186349 A1 | 7/2009 | Gunderson et al. | |
| 2010/0099576 A1 | 4/2010 | Comer et al. | |

FOREIGN PATENT DOCUMENTS

| | | |
|---|---|---|
| EP | 0 285 471 A1 | 10/1988 |
| EP | 0 296 078 A1 | 12/1988 |
| EP | 0 789 074 A1 | 8/1997 |
| EP | 1 451 302 B1 | 9/2004 |
| EP | 1 878 790 A1 | 1/2008 |
| EP | 1 974 718 A1 | 10/2008 |
| FR | 2 944 437 A1 | 10/2010 |
| WO | WO 01/12851 A2 | 2/2001 |
| WO | WO-01/92322 A1 | 12/2001 |
| WO | WO-02/070729 A2 | 9/2002 |
| WO | WO-03/066896 A2 | 8/2003 |
| WO | WO-2005/115421 A1 | 12/2005 |
| WO | WO-2006/063864 A2 | 6/2006 |
| WO | WO-2006/063865 A2 | 6/2006 |
| WO | WO-2006/084132 A2 | 8/2006 |
| WO | WO-2007/064305 A1 | 6/2007 |
| WO | WO-2007/111924 A2 | 10/2007 |
| WO | WO-2008/025847 A2 | 3/2008 |
| WO | WO 2010/053254 A1 | 5/2010 |
| WO | WO 2011/069913 A1 | 6/2011 |
| WO | WO-2011/073281 A1 | 6/2011 |

OTHER PUBLICATIONS

Mehul et al (Arch. Dermatol. Res. 2004, vol. 296, pp. 145-156).*
Both et al (Arch. Dermatol. Res., 2002, vol. 293, pp. 569-575).*
Narendran et al (Pediatric Research, 2010, vol. 67, No. 4 pp. 382-386).*
Hogan et al (Journal of Allergy, May 2012, vol. 2012, pp. 1-7) (Year: 2012).*
Varani et al (Toxicologic Pathology, 2007, vol. 35, pp. 693-701). (Year: 2007).*
Ahmad et al., "Cytochrome P450: A Target for Drug Development for Skin Diseases," The Society for Investigative Dermatology, Inc., vol. 123, 2004, pp. 417-425.
Bouwstra et al., "Structural Investigations of Human Stratum Corneum by Small-Angle X-Ray Scattering," The Society for Investigative Dermatology, vol. 97, No. 6, Dec. 1991, pp. 1005-1012.

(Continued)

*Primary Examiner* — Celine X Qian

(74) *Attorney, Agent, or Firm* — Rouget F. Henschel; Potomac Law Group, PLLC

(57) ABSTRACT

The present invention relates to a method for identifying biological markers for characterizing children's skin. The method of the invention thus makes it possible to identify molecular markers that are expressed differently in children's skin than in the skin of adults. The present invention therefore enables the skin to be characterized at the molecular level from birth and the changes thereof with age to be tracked.

12 Claims, 4 Drawing Sheets

(56)          References Cited

OTHER PUBLICATIONS

Figure 1A:
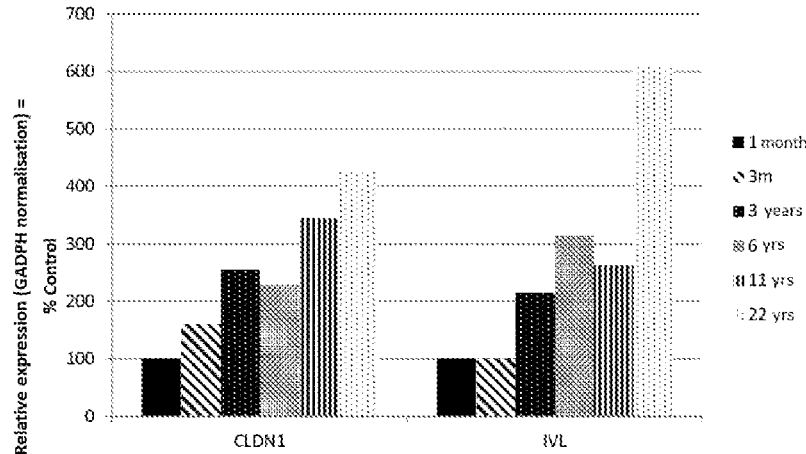

Costin et al., "Vaginal Irritation Models: The Current Status of Available Alternative and In Vitro Tests," ATLA, vol. 39, 2011, pp. 317-337.

Dayan, Nava "Stratum Corneum: The Role of Lipids and Ceramides," Cosmetics and Toiletries, vol. 121, No. 1, Jan. 2006, pp. 37-44.

Dongari-Bagtzoglou et al., "Development of a highly reproducible three-dimensional organotypic model of the oral mucosa," Nat Protoc, vol. 1, No. 4, 2006, pp. 1-15.

Downing et al., "Estimation of Sebum Production Rates in Man by Measuremtn of the Squalene Content of Skin Biopsies," Journal of Investigative Dermatology, vol. 77, No. 4, 1981, pp. 358-360.

Ebanks et al., "Mechanisms Regulating Skin Pigmentation: The Rise and Fall of Complexion Coloration" International Journal of Molecular Sciences, vol. 10, 2009, pp. 4066-4087.

Fluhr et al., "Functional skin adaptation in infancy—almost complete but not fully competent," Experimental Dermatology, vol. 19, No. 6, 2010, pp. 1-10.

Fuller et al., "The challenges of sequencing by synthesis," Nature Biotechnology, vol. 27, No. 11, Nov. 2009, pp. 1013-1023.

Gelardi et al., "Induction by xenobiotics of phase I and phase II enzyme activities in the human keratinocyte cell line NCTC 2544," Toxicology in Vitro, vol. 15, 2001, pp. 701-711.

Iwai et al., "The Human Skin Barrier Is Organized as Stacked Bilayers of Fully Extended Ceramides with Cholesterol Molecules Associated with the Ceramide Sphingoid Moiety," Journal of Investigative Dermatology, vol. 132, 2012, pp. 2215-2225.

Janmohamed et al., "Quantification and cellular localization of expression in human skin of genes encoding flavin-containing monooxygenases and cytochromes P450," Biochemical Pharmacology, vol. 62, 2001, pp. 777-786.

Jungersted et al., "Lipids and skin barrier function—a clinical perspective," Contact Dermatitis, vol. 58, 2008, pp. 255-262.

Katiyar et al., "Ultraviolet-B Exposure of Human Skin Induces Cycochromes P450 1A1 and 1B1," Th Society for Investigative Dermatology, Inc., vol. 114, No. 2, Feb. 2000, pp. 328-333.

Masukawa et al., "Comprehensive quantifi cation of ceramide species in human stratum corneum" Journal of Lipid Research, vol. 50, No. 8, 2009, pp. 1708-1719.

Nikolovski et al., "Barrier Function and Water-Holding and Transport Properties of Infant Stratum Corneum Are Different from Adult and Continue to Develop through the First Year of Life," Society for Investigative Dermatology, vol. 128, 2008, pp. 1728-1736.

Nissan et al., "Functional melanocytes derived from human pluripotent stem cells engraft into pluristratified epidermis," Proc. Natl. Acad. Sci., vol. 108, No. 36, 2011, pp. 14861-14866.

Nordstrom et al., "Measurement of Sebum Output Using a Lipid Absorbent Tape," Journal of Investigative Dermatology, vol. 87, No. 2, 1986, pp. 260-263.

Ponec et al., "Lipid and ultrastructural characterization of reconstructed skin models," International Journal of Pharmaceutics, vol. 203, 2000, pp. 211-225.

Ponec et al., "The Formation of Competent Barrier Lipids in Reconstructed Human Epidermis Requires the Presence of Vitamin C," Journal of Investigative Dermatology, vol. 109, No. 3, Sep. 1997, pp. 348-355.

Rainville et al., "Novel Application of Reversed-Phase UPLC-oaTOF-MS for Lipid Analysis in Complex Biological Mixtures: A New Tool for Lipidomics," Journal of Proteome Research, vol. 6, 2007, pp. 552-558.

Raza et al., "Glutathione S-Transferases in Human and Rodent Skin: Multiple Forms and Species-Specific Expression," Journal of Investigative Dermatology, vol. 96, 1991, pp. 463-467.

Robosky et al., "Quantitative evaluation of sebum lipid components with nuclear magnetic resonance" Journal of Lipid Research, vol. 49, 2008, pp. 686-692.

Shendure et al., "Next-generation DNA sequencing," Nature Biotechnology, vol. 26, No. 10, 2008, pp. 1135-1145.

Van Smeden et al., "LC/MS analysis of stratum corneum lipids: ceramide profi ling and discovery" Journal of Lipid Research, vol. 52, 2011, pp. 1211-1221.

Wei et al., "Screening of differential expression genes at human skin epidermal stem cells at different development stages by cDNA microarray technique," Chinese Journal of Burans, vol. 27, pp. 26-31, Feb. 1, 2011.

Martine et al., "Keratin 19 as a biochemical marker of skin stem cells in vivo and in vitro: Keratin 19 expressing cells are differentially localized in function of anatomic sites, and their number varies with donor age and culture stage," Journal of Cell Science, vol. 109, No. 5, Jan. 1, 1996.

Gilchrest, "Aging and photoaging affect gene expression in cultured human keratinocytes," Archives of Dermatology, vol. 130, No. 1, pp. 82-86, Jan. 1, 1994.

Fluhr et al., "Infant epidermal skin physiology: adaptation after birth," British Journal of Dermatology, vol. 166, No. 3, pp. 483-490, Mar. 1, 2012.

Agache et al., "Sebum levels during the first year of life," British Journal of Dermatology, vol. 103, No. 6, pp. 643-650, Dec. 1, 1980.

Kikuchi et al., "Impairment of Skin Barrier Function is not Inherent in Atopic Dermatitis Patients: A Prospective Study Conducted in Newborns," Pediatric Dermatology, vol. 23, No. 2, pp. 109-113, Mar. 1, 2006.

Perkins et al., "A noninvasive method to assess skin irritation and comprised skin conditions using simple tape absorption of molecular markers of inflammation," Skin Research and Technology, pp. 227-237, Nov. 1, 2001.

Coquette et al., "Analysis of interleukin-1alpha (IL-1alpha) and inerleukin-8 (IL-8) expression and release in in vitro reconstructed human epidermis for the prediction of in vivo skin irritation and/or sensitization," Toxicology In Vitro, vol. 17, No. 3, pp. 311-321, Jun. 1, 2003.

Weiss et al., "In vitro skin irritation: facts and future. State of the art review of mechanisms and models," Toxicology in Vitro, vol. 18, No. 3, pp. 231-243, Jun. 1, 2004.

Skin Ethic Laboratories, "Quality controls-Biological safety controls before tissue engineering," accessed from the Internet: http://www.skinethic.com/pageLibre000101ac.asp, Dec. 16, 2011.

International Search Report issued in application No. PCT/EP2013/064926 on Oct. 9, 2013.

Rosdy et al., "Production of basement membrane components by a reconstructed epidermis cultured in the absence of serum and dermal factors," British Journal of Dermatology, vol. 129, pp. 227-234, 1993.

Rosdy et al., "Structurally and Biochemically Normal Permeability Barrier of Human Epidermis Reconstituted in Chemically Defined Medium," Abstracts for the Society for Cutaneous Ultrastructure Research (SCUR) 23rd Annual Meeting, Brescia, Italy, Apr. 11-13, 1996 (Abstract).

Rosdy et al., "Terminal Epidermal Differentiation of Human Keratinocytes Grown in Chemically Defined Medium on Inert Filter Substrates at the Air-Liquid Interface," The Journal of Investigative Dermatology, vol. 95, No. 4, pp. 409-414, Oct. 1990.

Youn et al., "Cellular senescence induced loss of stem cell proportion in the skin in vitro," Journal of Dermatological Science, vol. 35, pp. 113-123, 2004.

De Benedetto et al., "Tight Junction Defects in Atopic Dermatitis," J. Allergy Clin. Immunol., vol. 127, No. 3, pp. 773-786, Dec. 2010.

Leclere-Bienfait et al., "Avocado perseose, a biomimetic patented active ingredient targeted to the needs of infants' skin," Journal of the American Academy of Dermatology, vol. 70, Issue 5, Supplement 1, p. AB143, May 2014.

* cited by examiner

Control                    + 0.4% SDS

+ Cleansing cream          Moisturising lotion

METHOD FOR IDENTIFYING MOLECULAR MARKERS OF CHILDREN'S SKIN

INTRODUCTION

The skin is a set of cells and macromolecules grouped together in the form of a resistant and flexible tissue, covering the entire body. The main function of the skin is that of creating a protective barrier against environmental damage while enabling some exchanges between the internal environment and the external environment. It is the site of numerous metabolic processes modulated by the physiological conditions of the body and environmental conditions. The skin consists of two joined layers: the epidermis and the dermis with which subcutaneous tissues may be associated.

The epidermis, the main role whereof is that of protecting the body, forms the uppermost layer of the skin and ensures the imperviousness of the skin and resistance thereof. Four separate cellular layers may be identified therein, a basal layer (stratum basalis), a spinous layer (stratum spinosum), a granular layer (stratum granulosum), and a corneal layer (stratum corneum). While various cell types coexist in the epidermis, keratinocytes represent the large majority (90%). The characteristic activity thereof is the synthesis of keratins representing 95% of total proteins in the epidermis. Keratins, fibrous proteins which are insoluble in water, form part of the corneal layer of the epidermis protecting the skin against external attacks (heat, cold, dehydration).

The epidermis is joined to the dermis by a region known as the dermal-epidermal junction or epidermal basement membrane. This structure ensures the adherence to the dermis to the epidermis and acts as a mechanical support partially responsible for skin tone. It is produced both by basal keratinocytes and by dermal fibroblasts and contains a high level of type IV collagen which is part of the anchor sheet joining the basement membrane to anchor sheets present in the papillary dermis.

The dermis, the inner layer of the skin, is a fibro-elastic connective tissue consisting of cells (fibroblasts) dispersed in a complex medium known as the extracellular matrix. This matrix consists of collagen and elastin fibres, glycoproteins (fibronectin and laminin) and proteoglycans (central protein+glycosaminoglycans or GAGS). The nature and quantity of these compounds determine the mechanical properties of the skin and are the source of the most visible physiopathological modifications of the skin surface obtained during ageing.

The hypodermis is the bottom most and thickest layer of the skin. It is invaginated in the dermis and is attached to the underlying dermis by collagen and elastin fibres. It essentially consists of a type of cell specialised in fat accumulation and storage, adipocytes. The adipocytes forming the hypodermis are cells grouped into separate lobules by connective tissue. It acts as an energy reserve, but also as thermal and mechanical protection.

Adaptation to extrauterine life is a process commencing at birth and continuing throughout the first year of life. The first months of postnatal life represent a period of functional reorganisation of the skin enabling physiological adaptation to the extrauterine environment.

For example, skin acidification increases after birth to reach at around one month values similar to those observed in adults. On the other hand, sebum secretion is significant at birth and decreases from the end of the first week to remain at a level below that measured in adults, until puberty (Fluhr et al., Exp Dermatol., 19(6): 483-492, 2010).

A recent clinical study associating conventional biometrological measurements with the Raman spectrometry technique (Fluhr et al., Br J Dermatol, 166(3): 483-90, 2012) demonstrated that the degree of hydration and water content of the corneal layer are lower at birth (1 to 15-day-old newborns), whereas the Natural Moisturising Factor (NMF) level is maximal. This level subsequently decreases whereas hydration stabilises. The authors hypothesise that the lower acidification and lower hydration of the skin could activate compensatory regulation mechanisms (with in particular significant NMF production), enabling the newborn to adapt to his/her new environment. In the same study, it was demonstrated that the NMF level in 6-month-old infants is found to be less than that observed in the adult group. This lower NMF level, demonstrated by another group (Nikolovski et al., J Invest Dermatol, 128: 1728-36, 2008) suggests that infants' skin exhibits some immaturity in respect of the ability thereof to take up water and regulate the mechanisms associated therewith, which would have an impact on the quality and competence of the barrier function.

Incomplete skin maturation may have significant clinical consequences. It is known for example that microbial pathogen growth is favoured by high pH values (Korting et al., Acta Derm Venereol., 70(5): 429-431, 1990). It is thus important not to use cleansers that would reduce skin acidification further in the first months of life.

Understanding the complex processes involved during the first stages of postnatal life would thus make it possible to identify active agents or combinations of active agents having a particularly suitable tolerance and efficacy for each age-group. However, we have no biological and molecular markers of skin changes in the first months, or first years of postnatal life.

Therefore, there is a need in the field for identifying markers which are specific for skin changes, from birth to adulthood.

LEGENDS OF THE FIGURES

FIG. 1: Progression of the expression of the barrier function genes CLDN1, IVL, KRT1, in reconstructed epidermises (A) and in keratinocytes (B) as a function of age. The expression level at 1 month was arbitrarily set to 100%.

FIG. 2: Progression of the expression of the stress response gene GP3X (A) and the innate immunity gene DEFB1 (B) as a function of age. The expression level at 1 month was arbitrarily set to 100%.

Figure 3:
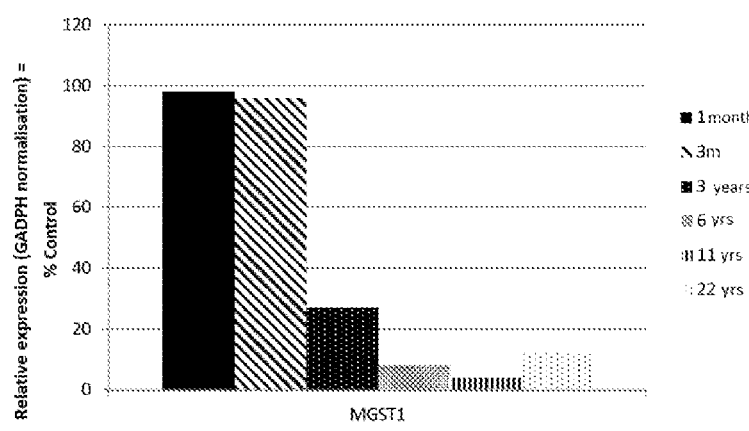

FIG. 3: Progression of the expression of the inflammation gene MGST1 in keratinocytes as a function of age. The expression level at 1 month was arbitrarily set to 100%.

Figure 4:
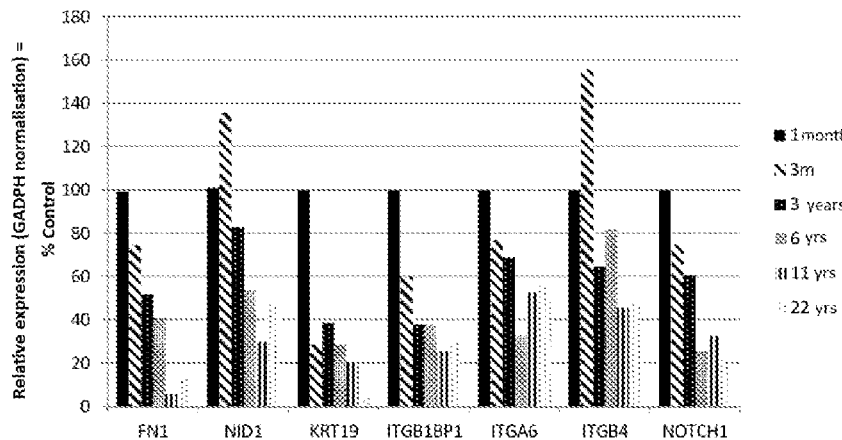

FIG. 4: Progression of the expression of stem cell genes: FN1, NID1, NOTCH1, KRT19, IGTB1P1, ITGA6 and ITGB4 in keratinocytes as a function of age. The expression level at 1 month was arbitrarily set to 100%.

Figure 5:
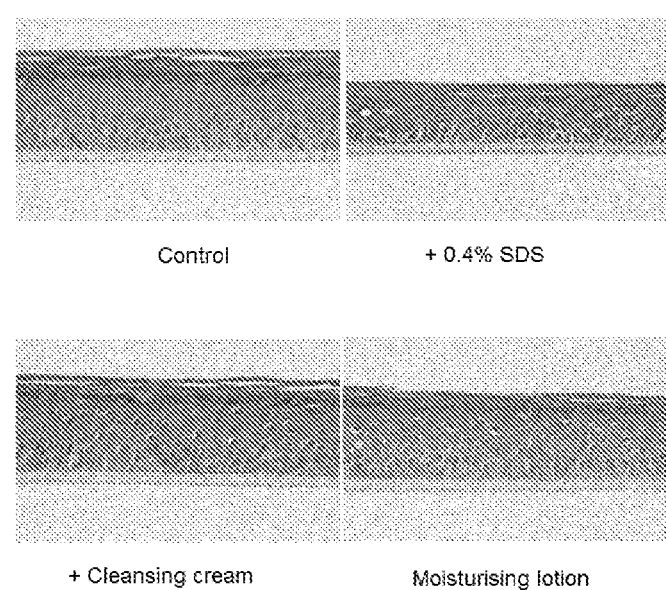

FIG. 5: Evaluation by means of histological analysis of the tolerance of baby products based on avocado perseose on reconstructed epidermises obtained from 1-month-old donors. The tissues included in paraffin were stained with haematoxylin and eosin.

DESCRIPTION OF THE INVENTION

The present invention aims at providing biological markers for characterising children's skin, from birth to puberty.

The method according to the invention thus makes it possible to identify molecular markers expressed differentially in children's skin, i.e. markers for which the expression is different in children's skin and in the skin of adults. The present invention is thus suitable for characterising the skin on a molecular level from birth and for monitoring the changes thereof over time.

The term "child", according to the invention, refers to a subject less than 16 years of age. As such, the category of children according to the invention includes newborns, between 0 and 1 month of age, infants, between 1 month and 2 years of age, and children per se, at least 2 years of age. A "newborn", as used herein, may equally well be born at full term or prematurely.

To remove any ambiguity, the term "child" used in the present application without any further clarification should be understood in the most general meaning thereof, i.e. as referring to a subject under 16 years of age. An "adult" according to the present invention is a subject who is not a child, i.e., in order words, a subject over 16 years of age.

Preferably, the method according to the invention may be used regardless of the ethnic or geographic origin of the skin, or the phototype thereof. It may thus be of Caucasian, African, Asian, South American, Melanesian or other origin; it may further have the phototype I, II, III, IV, V or VI, without affecting the invention. Indeed, the invention aims at identifying biological markers characterising any skin type and only dependent on the donor's age.

Moreover, those skilled in the art will readily realise that the teaching of the present invention may also be applied to mucosas. The mucosas are thin layers of epithelial tissue and underlying connective tissue, which are, like skin, at the interface between the internal and external environments. Furthermore, some of these mucosas are contiguous with the skin.

The invention thus relates to a method for identifying at least one biological marker characterising the skin of children under 16 years of age, said method comprising the following steps:

a) obtaining a sample of skin cells (A), said sample being obtained from a donor under 16 years of age, b) measuring the level of expression of a candidate biological marker in the sample from step a), and c) determining whether the candidate marker is a biological marker characterising the skin of children under 16 years of age.

A "biological marker" according to the invention is defined by at least one difference between the metabolism of the cells of children under 16 years of age and the metabolism of the cells of adults. Advantageously, the biological marker according to the invention is defined by at least one difference between the metabolism of the cells of newborns, infants and/or children from 2 to 16 years of age, and the metabolism of the cells of adults.

The term "biological marker characterising children's skin" according to the present invention refers to a marker specifically more expressed or less expressed in the skin of children under 16 years of age. In other words, a biological marker characterising children's skin is a marker wherein the expression varies with age and which is expressed differentially between children's skin and the skin of adults.

As described above, the skin changes functionally and structurally in the period after birth. In particular, variations of various parameters such as transepidermal water loss (TEWL), stratum corneum hydration or the pH of the skin surface are observed not only generally between 0 and 16 years of age, but also, more specifically, within this age range. As such, these parameters vary between newborns, infants and children between 2 and 16 years of age (Fluter et al., Exp Dermatol., 19(6): 483-492, 2010). In particular, specific variations of these parameters may be observed within each of these age-groups.

The term "biological marker characterising children's skin" as used in the present application thus also encompasses any biological marker which is more expressed or less expressed in newborns and/or in infants and/or in children between 2 and 16 years of age, than in adults. A marker characterising children's skin according to the invention may thus be expressed more or less than in adults in one or a plurality of these three categories, or even in the entire category of children under 16 years of age.

According to one more preferred embodiment, the donor of sample (A) is more specifically a donor between 0 and 1 month of age, between 1 month and 2 years of age or between 2 and 16 years of age. In other words, according to this embodiment, the donor of sample (A) is chosen from the group consisting of newborns, between 0 and 1 month of age, infants, between 1 month and 2 years of age, and children between 2 and 16 years of age.

In a first embodiment, it is possible to determine whether a candidate biological marker is a specific marker for children's skin by comparing the level of expression of the candidate marker in the sample of skin cells (A) and in a control sample of skin cells (B).

According to this first embodiment, the invention relates to a method for identifying at least one biological marker characterising children's skin, said method comprising the following steps:

a) obtaining at least one sample of skin cells (A), said sample being obtained from a donor under 16 years of age, b) obtaining at least one control sample (B) of skin cells, c) measuring the level of expression of a candidate biological marker in the sample from step a), d) measuring the level of expression of said candidate biological marker in the sample from step b), e) calculating the ratio between the level of expression of step a) and the level of expression of step b), and f) determining whether the candidate marker is a biological marker characterising newborns' or infants' skin.

According to one preferred embodiment, the invention relates to a method for identifying at least one biological marker characterising children's skin, said method comprising the following steps:

a) obtaining at least one sample of skin cells (A), said sample being obtained from a donor chosen from the group consisting of newborns, between 0 and 1 month of age, infants, between 1 month and 2 years of age, and children between 2 and 16 years of age, b) obtaining at least one control sample (B) of skin cells, c) measuring the level of expression of a candidate biological marker in the sample from step a), d) measuring the level of expression of said candidate biological marker in the sample from step b), e) calculating the ratio between the level of expression of step a) and the level of expression of step b), and f) determining whether the candidate marker is a biological marker characterising children's skin.

The control sample (B) according to the invention is a sample of skin cells obtained from a donor of known age. For example, the control sample (B) may be obtained from a child or an adult. More specifically, the control sample (B) may be obtained from a donor under 16 years of age or over 16 years of age. In one advantageous embodiment of the method according to the invention, the control sample (B) is obtained from a donor between 0 and 1 month of age, between 1 month and 2 years of age or between 2 and 16 years of age. It is thus possible to specify whether the biological marker characterising children's skin according to the invention is a marker characterising skin of a newborn under 1 month of age, skin of an infant between 1 month and 2 years of age, or skin of a child between 2 and 16 years of age.

It is clear that the ratio from step e) of the method according to the invention is dependent on the nature of the control sample (B). It is easily understood that if the donor of the control sample (B) is from the same age-group as the donor of sample (A), said ratio from step e) will be equal to approximately 1; on the other hand, if the donors of samples A and B are from two separate age-groups, then the ratio from step e) will be different from 1. As such, if sample (B) is obtained from an adult, a ratio between the levels of expression of the candidate marker in sample (A) and sample (B) greater than 1 indicates that said marker is specifically more expressed in children's skin. Similarly, also if sample (B) is obtained from an adult, a ratio between the levels of expression of the candidate marker in sample (A) and sample (B) less than indicates that said marker is specifically less expressed in children's skin.

In one preferred embodiment, the level of expression of the candidate marker is measured in at least two samples of skin cells, (A) and (A'), each of said samples being obtained from a donor under 16 years of age. More preferentially, each of said samples is obtained from a donor chosen from the group consisting of newborns, between 0 and 1 month of age, infants, between 1 month and 2 years of age, and children between 2 and 16 years of age. Advantageously, (A) and (A') belong to two different age-groups. More preferably, the control sample (B) is obtained from an adult donor.

It is thus possible to draw more accurate and more reliable conclusions in respect of the candidate marker. The term "skin sample" according to the invention refers to any sample containing skin cells. The skin samples according to the invention thus include fresh skin explants obtained directly from the patient, suspended skin cell cultures, monolayer skin cell cultures, bilayer skin cell cultures and tissue models, including reconstructed skin cultures and reconstructed mucosal cultures. As it is frequently difficult to work on fresh explants, it is particularly advantageous, within the scope of the present invention, to use skin cell cultures. Advantageously, the skin cells according to the invention include normal, healthy or diseased cells, or cells derived from lines. For example, the skin cells placed in culture may be cells obtained from a skin tissue explant. The term "explant" or "skin explant" as used herein refers to a sample of skin cells or tissue, which may be obtained for surgical purposes or to carry out tests.

In particular, an explant may be obtained during surgical excision. The term "excision" as used herein refers to a surgical procedure consisting of cutting (excising) a portion of varying width and depth of skin in order to treat a defect or growth thereof. Excision is performed either to remove a cancerous or suspected cancerous tumour, or to treat a benign skin defect which is unwanted, for functional or cosmetic reasons. An excision according to the invention includes for example skin samples obtained after plastic surgery (breast, abdominal plasty, lifting, foreskin removal, otoplasty, i.e. ear pinback, syndactyly or supernumerary fingers, etc.).

An example may also be obtained by means of biopsy. The term "biopsy" refers to a sample of skin cells or tissue taken for the purposes of analysis. A plurality of types of biopsy procedures are known and performed in the field. The most common types include (1) incisional biopsy, wherein only a tissue sample is taken; (2) excisional biopsy (or surgical biopsy) consisting of total ablation of a tumour growth, thus carrying out a therapeutic and diagnostic procedure, and (3) needle biopsy, wherein a tissue sample is taken with a needle, which may be wide or fine. Further types of biopsies exist, such as for example smears or curettage, and are also included in the present invention.

Alternatively, said skin cells may be obtained by stem cell differentiation (Guenou et al., Lancet, 374(9703): 1745-1753, 2009; Nissan et al., Proc. Natl. Acad. Sci., 108(36): 14861-14866, 2011; Kraehenbuehl et al., Nature Methods, 8: 731-736, 2011).

The skin cells according to the invention, whether obtained from a biopsy or obtained by stem cell differentiation, include at least one type of cells habitually present in the hypodermis, dermis and/or epidermis. These cells thus include, inter alia, keratinocytes, melanocytes, fibroblasts, adipocytes, endothelial cells, mast cells, Langerhans cells and/or Merkel cells. Preferentially, the skin cells according to the invention include at least keratinocytes and/or fibroblasts. More preferentially, the skin cells according to the invention include keratinocytes and/or fibroblasts.

Numerous skin cell culture methods are known to those skilled in the art. Any of these methods may be used to culture the skin cells according to the invention. Advantageously, the skin cells are cultured and/or stored under conditions maintaining, at least partially, a cell metabolism and/or cell functions. The culture of skin cells according to the invention thus includes equally well suspended skin cell cultures, monolayer skin cell cultures, bilayer skin cell cultures and tissue models, of which reconstructed skin cultures and reconstructed mucosal cultures.

For example, suspended skin cell cultures are performed routinely in a very large number of laboratories, for several decades. Similarly, monolayer or bilayer skin cell cultures have been known and used for a very long time.

Moreover, numerous tissue models, of which reconstructed skin models and reconstructed mucosal models (Rosdy et al., In Vitro Toxicol., 10(1): 39-47 1997; Ponec et al., J Invest Dermatol., 109(3): 348-355 1997; Ponec et al., Int J Pharm., 203(1-2): 211-225, 2000; Schmalz et al., Eur J Oral Sci., 108(5): 442-448, 2000; Black et al., Tissue Eng, 11(5-6): 723-733 2005; Dongari-Batgtzoglou and Kashleva, Nat Protoc, 1(4): 2012-2018, 2006; Bechtoille et al., Tissue Eng, 13(11): 2667-2679, 2007; Vrana et al., Invest Ophthalmol Vis Sci, 49(12): 5325-5331, 2008; Kinicoglu et al., Biomaterials, 30(32): 6418-6425, 2009; Auxenfans et al., Eur J Dermatol, 19(2): 107-113, 2009; Kinicoglu et al., Biomaterials, 32(25): 5756-5764, 2011; Costin et al., Altern Lab Anim, 39(4): 317-337, 2011; Auxenfans et al., J Tissue Eng Regen Med, 6(7): 512-518, 2012; Lequeux et al., Skin Pharmacol Physiol, 25(1): 47-55, 2012; EP 29 678; EP 285 471; EP 789 074; EP 1 451 302 B1; EP 1 878 790 B1; EP 1 974 718; US 2007/0148,771; US 2010/0,099,576; WO 02/070729; WO 2006/063864; WO 2006/0,63865; WO 2007/064305) are available to those skilled in the art and are included in the scope of the invention.

Advantageously, the tissue model includes reconstructed skin models and reconstructed mucosal models. Preferably, the reconstructed skin model is selected from the group including dermis models, essentially containing stromal cells, and more particularly fibroblasts, epidermis models essentially consisting of keratinocytes, hypodermis models, skin models including a dermis and an epidermis, and skin models including a dermis, an epidermis and a hypodermis. The models including at least one dermis, form connective type tissues, whereas the models including at one epidermis form stratified epithelia including characteristic layers of the tissue in question. For example, in the epidermis models, it is possible to identify a basal layer (stratum basalis), a spinous layer (stratum spinosum), a granular layer (stratum granulosum), and a corneal layer (stratum corneum). Furthermore, preferably, the reconstructed mucosal model according to the invention is a mucosal model of the mouth, gum, vagina or cornea.

Advantageously, said model is a connective type tissue model of dermal matrix comprising a matrix substrate preferably chosen from:

an inert substrate chosen from the group consisting of a semi-permeable synthetic membrane, in particular a semi-permeable nitrocellulose membrane, a semi-permeable nylon membrane, a Teflon membrane or sponge, a polycarbonate or polyethylene, polypropylene, semi-permeable polyethylene terephthalate (PET) membrane, an inorganic semi-permeable Anopore, cellulose acetate or ester (HATF) membrane, a semi-permeable Biopore-CM membrane, a semi-permeable polyester membrane, a polyglycolic acid membrane or film.

This group includes for example the SKIN$^2$™ model ZK1100 and DERMAGRAFT® and TRANSCYTE® dermal models (Advanced Tissue Sciences):

a cell culture-treated plastic (formation of a dermal sheet: Michel et al., In Vitro Cell. Dev Biol.-Animal, 35:318-326, 1999);

a gel or a membrane based on hyaluronic acid (HYALOGRAFT® 3D—Fidia Advanced Biopolymers) and/or collagen (such as for example an equivalent dermis or collagen lattices) and/or fibronectin and/or fibrin; this group includes for example the VITRIX® dermal model (Organogenesis);

an optionally surfaced porous matrix (for example an equivalent dermis), produced from collagen suitable for containing one or a plurality of glycosaminoglycans and/or optionally chitosan (EP0296078A1, WO 01/911821 and WO 01/92322).

This group also includes for example the Mimederm® dermal model (Coletica).

These matrix substrates comprise stromal cells, particularly fibroblasts.

Advantageously, said skin model is an epidermis model comprising a matrix substrate preferably chosen from:

an inert substrate chosen from the group consisting of a semi-permeable synthetic membrane, in particular a semi-permeable nitrocellulose membrane, a semi-permeable nylon membrane, a Teflon membrane or sponge, a polycarbonate or polyethylene, polypropylene, semi-permeable polyethylene terephthalate (PET) membrane, an inorganic semi-permeable Anopore, cellulose acetate or ester (HATF) membrane, a semi-permeable Biopore-CM membrane, a semi-permeable polyester membrane;

this group includes the Reconstructed epidermis models (SKINETHIC®) and the EPIDERM® model (Mattek Corporation);

a film or a membrane based on hyaluronic acid and/or collagen and/or fibronectin and/or fibrin.

In this group, particular mention may be made of the models: LASERSKIN® (Fidia Advanced Biopolymers), EPISKIN® (L'Oréal).

These models may be inoculated with fibroblasts in the dermal part.

These models, wherein fibroblasts may be optionally integrated, act as a substrate for keratinocyte inoculation and epidermis reconstruction. Advantageously, beside keratinocytes, pigment cells, immunocompetent cells, nerve cells are introduced; preferably, the immunocompetent cells are Langerhans cells.

Advantageously, said tissue model is a reconstructed skin or mucosal tissue model comprising a dermal or chorion matrix substrate, preferably chosen from:

an inert substrate chosen from the group consisting of a semi-permeable synthetic membrane, in particular a semi-permeable nitrocellulose membrane, a semi-permeable nylon membrane, a Teflon membrane or sponge, a polycarbonate or polyethylene, polypropylene, semi-permeable polyethylene terephthalate (PET) membrane, an inorganic semi-permeable Anopore, cellulose acetate or ester (HATF) membrane, a semi-permeable Biopore-CM membrane, a semi-permeable polyester membrane, said inert substrate optionally containing stromal cells, particularly fibroblasts;

a gel based on collagen and/or hyaluronic acid and/or fibronectin, and/or fibrin comprising stromal cells, particularly fibroblasts, an optionally surfaced porous matrix, produced from collagen suitable for containing one or a plurality of glycosaminoglycans and/or optionally chitosan, these porous matrixes incorporating stromal cells, particularly fibroblasts, a deepidermised dermis or dead dermis, of human or animal origin.

In this group, particular mention may be made of the MIMESKIN (Coletica), EPIDERM™, EPIAIRWAY™, EPIOCCULAR™, EPIORAL™, EPIGINGIVAL™, EPIVAGINAL™ (MatTek corporation), Human Corneal Epithelium (HCE), Human Oral Epithelium (HOE), Human Gingival Epithelium (HGE), Human Vaginal Epithelium (HVE) (SKINETHIC®), PHENION® Full Thickness Skin Model (Phenion) APLIGRAF® (Organogenesis), ATS-2000 (CELLSYSTEMS® Biotechnologie Vertrieb) models and Skin 2™ (ZK1200-1300-2000 Advanced Tissue Science).

Furthermore, models specifically intended for tissue therapy are available which may also be used within the scope of the present invention. Mention may be made of the EPIDEX (Modex Thérapeutiques), EPIBASE® (Laboratoire Genevrier), EPICELL™ (Genzyme), AUTODERM™ and Transderm™ TRANSDERM™ (Innogenetics) models.

The matrix substrate is then inoculated with keratinocytes to reconstruct the epidermis and eventually obtain a reconstructed skin.

Advantageously, the skin model used comprises a model wherein at least one complementary cell type has been incorporated, such as endothelial cells (CE) and/or immune cells such as lymphocytes, macrophages, mast cells, dendritic cells and/or adipose cells and/or skin appendages, such as hair on the body and head, sebaceous glands.

The candidate biological marker according to the invention is preferably a genetic marker, a protein marker, a lipid marker or a metabolic marker. For each of these types of markers, numerous methods are available to those skilled in the art for measuring the expression of said biological marker and thus identifying a difference in expression between the cells of children under 16 years of age and cells of adults.

In a first embodiment, said marker is a genetic marker or a protein marker.

In this case, the method according to the invention may comprise one or a plurality of intermediate steps between sampling the sample of skin cells and measuring the expression of the biological marker, said steps corresponding to the extraction from said sample of skin cells of an mRNA sample (or of the corresponding cDNA) or a protein sample. The preparation or extraction of mRNA (and the retrotranscription thereof to cDNA) or proteins from a cell sample are merely routine procedures well-known to those skilled in the art.

Once the mRNA (or corresponding cDNA) or protein sample is obtained, the expression of the marker, in respect of either the mRNA (i.e. in all the mRNA or cDNA present in the sample), or proteins (i.e. in all the proteins present in the sample), may be measured. The method used for this purpose is then dependent on the type of transformation (mRNA, cDNA or protein) and the type of sample available.

When the expression of the marker is measured in respect of mRNA (or corresponding cDNA), any technology commonly used by those skilled in the art may be applied. These technologies for analysing the level of gene expression, such as for example transcriptome analysis, include well-known methods such as PCR (Polymerase Chain Reaction, if using DNA), RT-PCR (Reverse Transcription-PCR, if using RNA) or quantitative RT-PCR or nucleic acid arrays (including DNA arrays and oligonucleotide arrays) for a greater throughput.

The term "nucleic acid arrays" as used herein refers to a plurality of different nucleic acid probes attached to a substrate, which may be a microchip, a glass slide, or a bead having the size of a microsphere. The microchip may consist of polymers, plastics, resins, polysaccharides, silica or a material based on silica, carbon, metals, inorganic glass, or nitrocellulose.

The probes may be nucleic acids such as cDNA ("cDNA array"), mRNA ("mRNA array") or oligonucleotides ("oligonucleotide array"), said oligonucleotides typically being suitable for having a length between approximately 25 and 60 nucleotides.

To determine the expression profile of a particular gene, a nucleic acid corresponding to all or part of said gene is labelled, then placed in contact with the array under hybridisation conditions, resulting in the formation of complexes between said labelled target nucleic acid and the probes attached to the chip surface which are complementary to this nucleic acid. The presence of labelled hybridised complexes is then detected.

These technologies are suitable for monitoring the level of expression of one gene in particular or of a plurality of genes or even all the genes of the genome (full genome or full transcriptome) in a biological sample (cells, tissues, etc.). These technologies are used routinely by those skilled in the art and there is thus no need to detail them herein. Examples of embodiments of the invention based on the analysis of gene expression (cDNA arrays) and on quantitative PCR are described in the experimental section.

Alternatively, it is possible to use any current or future technology suitable for determining gene expression on the basis of the quantity of mRNA in the sample. For example, those skilled in the art can measure the expression of a gene by hybridisation with a labelled nucleic acid probe, such as for example by means of Northern Blot (for mRNA) or Southern Blot (for cDNA), but also using techniques such as the serial analysis of gene expression (SAGE) method and the derivatives thereof, such as LongSAGE, SuperSAGE, DeepSAGE, etc. It is also possible to use tissue chips (also known as TMAs: "tissue microarrays"). The tests usually used with tissue arrays include immunohistochemistry and fluorescent in situ hybridisation. For the analysis in respect of mRNA, the tissue arrays may be coupled with fluorescent in situ hybridisation.

Finally, it is possible to use mass parallel sequencing to determine the quantity of mRNA in the sample (RNA-Seq or "Whole Transcriptome Shotgun Sequencing"). For this purpose, a plurality of mass parallel sequencing methods are available. Such methods are described in, for example, U.S. Pat. Nos. 4,882,127, 4,849,077; 7,556,922; 6,723,513; WO 03/066896; WO 2007/111924 US 2008/0020392; WO 2006/084132; US 2009/0186349; US 2009/0181860; US 2009/0181385; US 2006/0275782; EP-B1-1141399; Shendure & Ji, Nat Biotechnol., 26(10): 1135-45. 2008; Pihlak et al., Nat Biotechnol., 26(6): 676-684, 2008; Fuller et al., Nature Biotechnol., 27(11): 1013-1023, 2009; Mardis, Genome Med., 1(4): 40, 2009; Metzker, Nature Rev. Genet., 11(1): 31-46, 2010.

When the expression of the marker is measured in respect to protein, it is possible to use specific antibodies, particularly in well-known technologies such as immunoprecipitation, immunohistology, Western Blot, Dot Blot, ELISA or ELISPOT, protein arrays, antibody arrays, or tissue arrays coupled with immunohistochemistry. Other techniques which may be used include FRET or BRET techniques, microscopy or histochemistry methods, particularly including confocal microscopy and electron microscopy methods, methods based on the use of one or a plurality of excitation wavelengths and a suitable optical method, such as an electrochemical method (voltammetry and amperometry techniques), atomic force microscopy, and radiofrequency methods, such as multipolar, confocal and non-confocal resonance spectroscopy, detection of fluorescence, luminescence, chemoluminescence, absorbance, reflectance, transmittance, and birefringence or refractive index (for example, by means of surface plasmon resonance, by ellipsometry, by means of the resonant mirror method, etc.), flow cytometry, radioisotopic or magnetic resonance imaging, analysis by means of polyacrylamide gel electrophoresis (SDS-PAGE); by means of HPLC-Mass spectrophotometry, by means of liquid chromatography/mass spectrophotometry/mass spectrometry (LC-MS/MS). All these techniques are well-known to those skilled in the art and it is not necessary to detail them herein.

Preferentially, the candidate genetic or protein marker is selected from the group including cell metabolism markers, stress response markers, inflammation markers, immunity markers, apoptosis markers, cell growth/proliferation and cycle markers, cell signalling markers, migration and differentiation markers, epidermal barrier markers, adhesion markers and markers of pluripotent skin stem cells.

Those skilled in the art seeking to determine the class to which a genetic or protein marker belongs can easily consult the relevant scientific literature or refer to public databases such as, for example, those contained in the National Center for Biotechnology Information website www.ncbi.nim.nih-.gov/guide).

More preferentially, said cellular energy metabolism marker is IGFL3 (IGF-like family member 3), said stress response marker is GP3X (glutathione peroxidase 3), said inflammation marker is selected from the group consisting of MGST1 (microsomal glutathione S-transferase 1), IL-1 (interleukin-1) and IL-8 (interleukin 8), said immunity marker is selected from the group consisting of DEFB1 and DEFB4 (defensin beta1 and beta4), said cell cycle marker is CDKN1 (cyclin-dependent kinase inhibitor), said differentiation marker is BARX2 (BARx Homeobox 2) or SCEL (sciellin), said epidermal barrier marker is selected from the group consisting of CLDN1 (claudin 1), IVL (involucrin), and KRT1 (keratin 1), said adhesion marker is CADM1 (cell adhesion molecule 1) and/or said pluripotent skin stem cell marker is selected from the group consisting of FN1 (fibronectin 1), NID1 (nidogen 1), NOTCH1 (Notch homolog 1, translocation-associated), KRTI9 (keratin 19), ITGB1BP1 (integrin beta1 binding protein), ITGA6 (integrin alpha6) and ITGB4 (integrin beta4).

The gene CLDN1 (NM_021101) codes for the protein claudin 1 which is one of the most important components of tight junctions. Involucrin, coded by the gene IVL (NM_005547) is involved in the formation of the corneal envelope of corneocytes. The gene KRT1 (NM_006121) codes for keratin 1 forming the intracellular network of keratinocytes. BARX2 (NM_003658) codes for a transcription factor regulating adhesion during the formation of the epidermis and the differentiation thereof. Finally, the product of the gene SCEL (NM_001160706; NM_003843; NM_144777), sciellin, is involved in regulating corneal envelope proteins.

GPX3 (NM_002084) codes for glutathione peroxidase which has a defence role against oxidative stress. DEFB1 (NM_005218) and DEFB4 (NM_004942) coding for beta defensins are more specifically innate immunity genes, the products whereof belong to the same family of antimicrobial peptides.

The gene MGST1 (NM_145792; NM_001267598; NM_145764; NM_001260511; NM_020300; NM_001260512; NM_145791) codes for an inflammation protein, microsomal glutathione transferase, which is involved in inflammation mediator production.

The genes IL-1 (NM_000575; NM_000576; NM_001243211; NM_000577) and IL-8 (NM_000584) code for two cytokines which are significant inflammation mediators.

FN1 (NM_212482; NM_002026; NM_212476; NM_212478; NM_212474; NM_054034) codes for fibronectin 1, involved in the stem cell adhesion process. The gene NOTCH1 (NM_017617) is involved in stem cell maintenance. The protein nidogen 1 or entactin, coded by the gene NID1 (NM_002508), is a component of the basement membrane involved in stem cells, in interaction with the matrix. The protein keratin 19, coded by the gene KRT19 (NM_002276) is a member of the keratin family which is specifically expressed in stem cells. Finally, ITGB1BP1 (NM_022334; NM_004763), ITGA6 (NM_001079818; NM_000210), ITGB4 (NM_000213; NM_001005731; NM_001005619) code respectively for integrin beta 1 binding protein, integrin alpha 6 and integrin beta 4, all essential for stem cell adhesion to the matrix.

Lamellar bodies situated in the upper layer of the stratum granulosum (granular layer), designated "Odland bodies", contain sterols, phospholipids and glucosylceramides, and specific hydrolases. These enzymes convert phospholipids and glucosylceramides into free fatty acids and ceramides which form, with cholesterol and cholesterol sulphate, an intercellular lamellar bilayer. Said layer helps protect the skin against external attacks and maintain a satisfactory intraepidermal water layer (Jungerstend et al., Contact Dermitis, 58(5): 255-262, 2008). However, this skin barrier function changes with age, particularly between birth and adulthood (Fluhr et al., Exp Dermatol., 19(6): 483-492, 2010). Besides the lipids in the intercellular lamellar bilayer, the skin produces and secretes a mixture of fat substances referred to as sebum comprising mono-, di- and triglycerides, free fatty acids, waxes and esterified waxes, squalenes and sterols. Sebum secretion varies from birth to adulthood. As such, this secretion increases during the first week after birth, and then decrease before increasing again at pre-puberty (Fluhr et al., Exp Dermatol., 19(6): 483-492, 2010).

According to a further embodiment, the biological marker according to the invention is thus a lipid marker.

In particular, the lipid marker according to the invention may be a corneal layer lipid marker or a sebum lipid marker.

Advantageously, the lipid marker according to the invention is a corneal layer lipid marker. Preferably, said lipid is chosen from phospholipids, ceramides, sterols and free fatty acids.

The term "phospholipid" as used herein refers to any lipid comprising a phosphate group. Advantageously, the phospholipids according to the invention are chosen from the group consisting of phosphoglycerides and sphingomyelins. A "phosphoglyceride" according to the invention is a glycerol ester wherein two alcohol functions are esterified by fatty acids and the third by a phosphoric acid. Advantageously, the fatty acids are saturated or unsaturated and contain 14 to 20 carbon atoms. Preferably, a phosphoglyceride according to the invention is chosen from the group consisting of phosphatidylethanolamine, phosphatidylcholine, phosphatidylserine and phosphatidylinositol. The term "sphingomyelin" refers to a molecule consisting of a long chain base (sphingosine or dihydrosphingosine), a fatty acid amidifying the amine function and a phosphate esterifying the primary alcohol function and in turn esterified by an amino alcohol (choline).

The term "sterol" herein refers to a lipid belonging to a subgroup of steroids having a free hydroxyl group, and any derivative of said lipid. The sterols may be of natural or synthetic origin. Advantageously, the sterols according to the invention are chosen from cholesterol or cholesterol sulphate.

A "ceramide" according to the invention is a lipid obtained from the amidification reaction of sphingosine and a fatty acid. A ceramide thus consists of a sphingosine or phytosphingosine base bound by an amide bond to α-hydroxy, ω-hydroxy or non-hydroxy acids having variable hydrophobic chain lengths. In the human stratum corneum, 9 ceramide classes, referred to as CER 1 to 9, have been identified (see for example Dayan, Cosm & Toil, 121(1): 37-44 2006; Jungerstend et al., Contact Dermitis, 58(5): 255-262 2008; Farwick et al., Cosm & Toil, 124(2): 63-72; Masukawa et al., J Lipid Res., 50(8) 1708-1719, 2009). The ceramide according to the invention is chosen more preferentially in the group consisting of said ceramides CER1 to 9.

The lipid marker according to the invention may also be a sebum lipid marker. Preferably, such a lipid marker is chosen from the group consisting of mono-, di- and triglycerides, free fatty acids, waxes and esterified waxes, squalenes and sterols.

"Glycerides", or acylglycerols or glycerolipids, are esters of fatty acids and glycerol. Based on whether they are esterified by one, two or three fatty acid chains, they are referred to as mono-, di- or triglycerides.

According to the invention, the term "waxes" refers to fat substances consisting of various cerides, alcohols and free fatty acids and frequently long-chain saturated hydrocarbons. The term "ceride" refers to herein monoesters of fatty acids and long-chain aliphatic alcohols; ceride alcohols are generally primary alcohols, with an even number of carbons, saturated and non-branched, whereas the length of the carbon chains varies from 14 to 30 carbons for the fatty acid and from 16 to 36 carbons for the fatty alcohol.

A squalene, according to the invention, is a triterpene, isoprenoid with thirty carbon atoms and fifty hydrogen atoms, having the formula: (E) 2,6,10,15,19,23-Hexamethyl-2,6,10,14,18,22-tetracosahexene.

Finally, the skin surface is covered with a protective film enabling the skin to maintain the hydration thereof and protect itself against external attacks. This surface skin film comprises, inter alia, a hydrolipidic film, essentially consisting of sweat, water, sebum and other lipids. These include ceramides, triglycerides and fatty acids, in approximately equal proportions. The lipids of the hydrolipidic film have a specific three-dimensional structure.

Numerous methods are available to those skilled in the art for measuring the lipid content in a sample of skin cells. These methods include, inter alia, high pressure liquid chromatography (HPLC, see for example Sullivan et al., Arch Ophthalmol., 120(12): 1689-99, 2002), for example coupled with an evaporative light scattering detector (HPLC-ESD, see Nordbäck et al., J. High Resolut. Chromatogr., 22: 483-486, 1999; Torres et al., J. Chromatogr. A., 1078: 28-34, 2005); thin-layer chromatography (TLC, for example Downing et al., J Invest Dermatol., 77(4): 358-360, 1981; Nordstrom et al., J Invest Dermatol, 87(2): 260-263, 1986); nuclear magnetic resonance (NMR, see for example Robosky et al., J Lipid Res., 49(3): 686-692, 2008); in vivo confocal Raman microspectroscopy; mass spectrometry, gas chromatography coupled with mass spectrometry (GC-MS, see O'Neill et al., J Chromatogr Sci., 14(1): 28-36, 1976); ultra-performance liquid chromatography (UPLC, see Rainville et al., J Proteome Res., 6(2): 552-558, 2007; Castro-Perez et al., J Proteome Res., 10(9): 4281-4290, 2011). It is also possible to analyse the organisation of these lipids in the skin and more particularly in the stratum corneum (or corneal layer), lamellar or lateral organisation, using techniques such as X-ray diffraction (Bouwstra et al., J Invest Dermatol., 97(6): 1005-1012, 1991; van Smeden et al., J Lipid Res., 52(6): 1211-1221, 1991) or using Fourier transform infrared spectroscopy (Gorcea et al., Int J Pharm. Nov. 10, 2011.) or using electron microscopy morphometric analysis (Daehnhardt-Pfeiffer et al., Skin Pharmacol Physiol., 25(3): 155-161, 2012) or using an electron microscopy analysis of a vitreous skin section combined with a molecular analysis (Iwai et al., J Invest Dermatol., Apr. 26, 2012).

According to a further embodiment of the invention, the candidate biological marker is a metabolic marker.

The term "metabolic marker" according to the present invention refers to markers involved in the general regulation of the metabolic processes of the skin, including the energy metabolism. The "metabolism" according to the invention corresponds to the set of molecular and energy transformations taking place continuously in skin cells. In other words, the term "metabolism" comprises herein any reactions whereby, for example, skin cells produce and use energy, maintain the identity thereof, reproduce, eliminate toxic compounds, etc.

The metabolic markers according to the invention notably include skin metabolites present differentially in the skin of children under 16 years of age, and more particularly newborns, infants and/or children of 2 to 16 years of age, when compared to the skin of adults. In the context of the present invention, "differential" refers to a level different in the measured sample than in the control sample. For example, a metabolite present differentially in the skin of children (or newborns, infants and/or children of 2 to 16 years of age) may be present in greater quantities in said children's skin than in the skin of adults. Alternatively, this metabolite may be present in smaller quantities in the skin of children (or newborns, infants and/or children of 2 to 16 years of age) than in the skin of adults.

The metabolic markers of the skin are well-known to those skilled in the art. They are for example described in Fluhr et al. (Exp Dermatol., 19(6): 483-492, 2010) or in Jungerstend et al. (Contact Dermitis, 58(5): 255-262, 2008). The biological markers according to the invention include epidermis construction and skin barrier function markers, such as, for example, eleidin or natural moisturising factors, or NMF. These are a mixture of hygroscopic substances having the property of retaining water (Fluhr et al., Exp Dermatol., 19(6): 483-492, 2010). Some of these NMF are obtained from the proteolysis of filaggrin according to a cascade of reactions involving enzymes such as in particular caspase 14 and peptidylarginine deiminase (PAD1). Further epidermal and dermal hygroscopic molecules such as hyaluronic acid help maintain a satisfactory water level and give the skin suppleness and volume. This glycosaminoglycan is synthesised by hyaluronan synthase type 1, 2 or 3, whereas it is degraded by hyalurinodases. The skin barrier function is essentially provided by the corneal layer and involves both intercellular lipids and corneocytes which both have a structural and functional role. Enzymes accompany the synthesis and maturation of these key lipids such as e.g, betaglucocerebrosidase and acid sphingomyelinase; further enzymes also carry out the organisation of the proteins forming corneocytes such as transglutaminase in particular. Once all the epidermal layers have been formed and the differentiation is complete, the desquamation process enables the elimination of corneocytes involving enzymes such as kallikreins 5 and 7. Under the epidermis, the dermis may be subject to reorganisation or remodelling of the extracellular matrix involving metalloproteinases and elastase.

Furthermore, it is known that the hormone concentration of skin varies with age. According to a further aspect of the invention, the metabolic markers of the skin are thus hormones, and in particular sex hormones/steroids such as oestrogens and androgens (for example oestradiol, progesterone and testosterone), adrenal gland hormones which are also steroids (for example DHEA, cortisol), thyroid hormones (for example thyroxine and triodothyrosine), glucocorticoids, (for example cortisol or hydrocortisone), neurohormones (for example proopiomelanocortin and adrenocorticotrophic hormone), etc.

The metabolic markers according to the invention may also include enzyme activities such as antioxidant enzymes, particularly catalase, glutathione peroxidase, superoxide dismutase, etc.

The metabolic markers of the skin also include enzyme activities associated with eliminating exogenous toxic compounds (or xenobiotics) from cells. It has been known for a long time that this elimination process, or biotransformation, generally includes two steps: a functionalisation step or phase I, and a conjugation step or phase II. Biotransformation thus makes use of two types of activities, phase I enzymes and phase II enzymes. These two types of enzyme activity are present in skin cells and are included in metabolic markers of skin (see for example Ahmad and Mukhtar, J Invest Dermatol., 123: 417-425, 2004; Cheung et al., J Dermatol Sci, 31: 9-19, 2003; Gelardi et al., Toxicol in Vitro, 15: 701-711, 2001; Hotchkiss S. A. M., 1998. Dermal metabolism. In: Roberts, M. S., Walters K. A. (Eds.) Dermal Absorption and Toxicity Assessment. Marcel Dekker Inc, New York, pp. 43-101; Janmohamed et al Biochem Pharmacol, 62: 777-786, 2001; Katiyar et al., J Invest Dermatol, 114: 328-333, 2000; Moss et al., Food Chem Toxicol, 38: 361-370, 2000; Oesch et al., Drug Metab Rev, 39: 659-698, 2007; Oesch et al., Biochem Pharmacol, 27: 17-20, 1978;

Pillai et al., Pharm Res, 21: 1146-1152, 2004; Raza et al., J Invest Dermatol, 96: 463-467, 1991; Nordquist and Oreland, J Neural Transm, 114: 713-716, 2007).

Advantageously, the metabolic marker of the skin according to the invention is a phase I enzyme. The term "phase I enzyme" refers to an enzyme suitable for performing oxidation. Preferably, the phase I enzyme according to the invention is an enzyme of the cytochrome P450 family, a flavin mono-oxygenase, a monoamine oxidase, an alcohol dehydrogenase, an aledehyde dehydrogenase, an esterase or an epoxide hydrolase. The term "cytochrome P450" as used herein refers to an enzyme consisting of a protein part, apoprotein, and a prosthetic group consisting of a protoporphyrin bound with an iron atom by four covalent bonds, said enzyme being involved in the oxidative metabolism of very diverse molecules. A "flavin mono-oxygenase" according to the invention is an enzyme fixing flavin adenine dinucleotide (FAD) and catalysing with the aid of NADPH, the oxygenation of nucleophilic molecules such as phosphorus, nitrogen or sulphur which are present in numerous exogenous compounds. The term "monoamine oxidase" refers to herein to an enzyme catalysing the oxidative deamination of primary amines to form aldehydes. "Alcohol or aldehyde dehydrogenases" are enzymes catalysing the oxidation of alcohol functions to aldehydes or ketones, and then to carboxylic acids. The term "esterase" according to the invention refers to enzymes involved in the hydrolysis of ester functions and thus releasing the corresponding alcohol and carboxylic acid functions. An "epoxide hydrolase" according to the invention is an enzyme carrying out the detoxification of epoxides by means of hydration and formation of diols. More preferentially, the phase I enzyme according to the invention is a cytochrome P450 chosen from CYP1A, CYP2C and CYP3A.

Alternatively, the metabolic marker of skin according to the invention is a phase II enzyme. The term "phase II enzyme" refers to an enzyme suitable for carrying out conjugation. Preferentially, a "phase II enzyme" according to the invention is a transferase, i.e. an enzyme catalysing the reaction between a nucleophilic substrate (alcohol, carboxylic acid, amine or thiol) and an electrophilic hydrosoluble substrate. More preferentially, the phase II enzyme according to the invention is a UDP-glucuronyltransferase, a sulphotransferase, a glutathione-S-transferase or an N-acetyltransferase. The term "UDP-glucuronyltransferase" as used herein refers to an enzyme suitable for fixing glucuronic acid onto an oxygen, nitrogen or sulphur atom of a molecule for forming glucuronide compounds. A "sulphotransferase" according the invention catalyses the addition to a functionalised molecule of a sulphate group in activated form, said sulphate group being given by 3'-phosphoadenosine-5'-phosphosulphate (PAPS). "Glutathione-S-transferases" (GSTs) according to the invention are a superfamily of enzymes catalysing the conjugation between reduced glutathione and electrophilic xenobiotics (aromatic compounds, epoxides, etc.). The term "N-acetyltransferase" (NAT) according to the invention refers to an enzyme responsible for the biotransformation by means of acetylation of various compounds (aromatic amines, sulphonamides, hydrazines, etc.).

The metabolic markers of skin according to the invention also include skin pigmentation-related markers.

Skin pigmentation is the result of the presence of melanin grains in keratinocytes. According to a first aspect, the skin pigmentation-related marker according to the invention is thus a melanin. Melanin is the main pigment in skin: the melanin level in skin determines the colour thereof (light, dark, etc.) and provides a variable degree of protection with respect to ultraviolet radiation. The term "melanin" as used herein encompasses both pheomelanin and eumelanin. "Pheomelanin" or "phemelanin" according to the invention is a yellow or red-brown pigment, essentially consisting of sulphur-rich benzothiazine compounds. "Eumalenin" refers herein to a highly heterogeneous copolymer consisting of DHI (5,6-dihydroxyindole) and DHICA (5,6-dihydroxyindole-2-carboxylic acid) units and forming a brown-black pigment, which is sulphur-depleted. Eumelanin and pheomelanin are well-known to those skilled in the art (see for example Bertolo et al., m/s, 17(2): 177-185, 2001; Ito and Wakamatsu, Pigment Cell Res, 16(5): 523-531, 2003; Ebanks et al., Int J Mol Sci, 10: 4066-4087, 2009).

According to a second aspect, the skin pigmentation-related marker according to the invention is an enzyme activity regulating melanin synthesis. Advantageously, said marker is a "tyrosinase" type activity. A tyrosinase activity according to the invention is an enzyme activity capable of catalysing the hydroxylation of tyrosine to dihydroxyphenylalanine (DOPA) and of DOPA to dopaquinone. An example of tyrosinase corresponds for example to the product of the albino locus of mice, and to the homologues thereof in further mammalian species. The reaction catalysed by tyrosinase is common to the biosynthesis of eumelanins and to that of pheomelanin (Bertolo et al., m/s, 17(2): 177-185, 2001; Ebanks et al., Int J Mol Sci, 10: 4066-4087, 2009).

Alternatively, the skin pigmentation-related marker is an enzyme activity specific for pheomelanin or eumelanin synthesis. Preferentially, said enzyme activity is specific for eumelanin synthesis. More preferentially, said enzyme activity is a DHICoxidase (or TRP-1 or TYRP1 or gp75) type of DOPAchrome tauomerase (or TRP-2 or TYRP2) type activity. DHICAoxidase denotes herein an enzyme activity capable of catalysing the oxidation of 5,6-dihydroxyindole-2-carboxylic acid (DHICA) to indole 5,6-quinone-2-carobxylic acid. Such an activity is, for example, carried by a homologous protein of the product of the brown mouse locus. DOPAchrome tautomerase is an enzyme activity capable of catalysing the oxidation of dopachrome to DHICA which is, for example, coded by a homologous gene of the slaty mouse gene.

It is understood herein that the products of the reactions catalysed by the various enzyme activities according to the invention are also covered by the definition of skin pigmentation markers. As such, DOPA, dopaquinone, leucodopachrome, dopachrome, DHI, indole-5,6-quinone, DHICA, indole 5,6-quinone-2-carboxylic acid are all biological markers of skin according to the invention, like cysteinyl-dopa and 1,4-benzothiazinylalanine (see for example FIG. 1 of Bertolo et al., m/s, 17(2): 177-185, 2001).

The hypodermis includes cells specialised in the synthesis and storage of triglycerides, adipocytes. The hypodermis may thus include white adipocytes, forming white fat or white adipose tissue, and brown adipocytes, forming brown fat or brown adipose tissue. The latter is particularly present at the start of life.

The biological markers according to the invention also include adipocyte-related markers. In particular, the markers according to the invention include the ratio between the number of white adipocytes and the number of brown adipocytes. White fat adipocytes are spherical cells, approximately one hundred micrometres in diameter, wherein the cytoplasm contains a large single lipid vacuole (triglycerides), surrounded by a thin cytoplasmic ring containing a Golgi apparatus, granular endoplasmic reticulum, smooth endoplasmic reticulum and mitochondria. Unlike white adipocytes, brown adipocytes have a central nucleus and a cytoplasm filled with many small lipid vacuoles (the cell is described as multilocular) and mitochondria.

White adipocytes secrete numerous peptides, collectively known as adipocytokines (Avram et al., J Am Acad Dermatol, 53(4): 671-683, 2005) which include, inter alia, leptin, adipsin, adiponectin, and the protein ASP (acylation stimulating protein). In one preferred embodiment, the adipocyte-related markers according to the invention are adipocytokines; more preferentially, said markers are chosen from leptin, adipsin, adiponectin, resistin, and the protein ASP. The term "leptin" refers herein to a protein of 16 kDa, coded by the Ob gene, and regulating fat reserves in the body and appetite by controlling the satiety sensation. Advantageously, the leptin has the peptide sequence represented by NP_000221.1. The term "adipsin" or "Factor D" or "complement factor D(CFD)" refers to a protein of 253 residues having a serine protease activity and coded by the CFD gene. Advantageously, the adipsin has the peptide sequence represented by NP_001919. The term "adiponectin" or "AdipoQ", "Acr30" (adipocyte complement-related protein of 30 kD), "APM1" (adipose most abundant gene transcript 1), or "GBP28" (gelatin-binding protein of 28 kD), refers to a protein of 244 amino acids involved, inter alia, in regulating the lipid and glucose metabolism. Advantageously, this protein has the amino acid sequence represented by NP_001171271.1. "Resistin" or "ADSF" (adipose tissue-specific secretory factor) or "XCP1" (C/EBP-epsilon-regulated myeloid-specific secreted cysteine-rich protein) is a protein having 108 amino acids coded by the RSTN gene. Advantageously, the resistin protein has the protein sequence NP_0011803.1. The protein "ASP", according to the invention, is a cleavage product of complement C3 factor (NP_000055.2) which is specific for adipocytes and regulating glucose intake into these cells and non-esterified fatty acid storage.

White adipocytes may release energy in the form of free fatty acids from stored triglycerides: this is lipolysis. In a further preferred embodiment, the adipocyte-related markers according to the invention include enzyme activities associated with lipolysis, i.e. with triglyceride hydrolysis. Preferentially, a said enzyme activity is a lipase type activity. A "lipase" according to the invention is a hydrosoluble enzyme capable of hydrolysing ester functions and specialised in the transformation of triglyceride into glycerol and fatty acids. The lipase according to the invention is more preferentially a hormone-sensitive lipase, a monoglyceride lipase or an adipose triglyceride lipase (Lafontan and Langin, Prog Lipid Res, 48(5): 275-297, 2009). The "hormone-sensitive lipase" as used herein is an enzyme capable of hydrolysing triglycerides into diglycerides and diglycerides into monoglycerides and wherein the activity is regulated by the intracellular cAMP level via phosphorylation by protein kinase A (PKA). An example of hormone-sensitive lipase corresponds to human HSL protein, wherein the sequence is given by NP_005348.2. The term "monoglyceride lipase" denotes an enzyme associated with the membrane capable of hydrolysing monoglycerides into glycerol and fatty acid. Human monoglyceride lipase corresponds to the protein MAGL, MGL or MGLL (NP_001243514). An "adipose triglyceride lipase" according to the invention is an enzyme capable of hydrolysing triglycerides, but only triglycerides (and thus not diglycerides and/or monoglycerides), and is not phosphorylated by PKA. For example, reference may be made to human ATGL protein, which has the sequence corresponding to the identification number NP_065109.1. As mentioned above, the biological markers according to the invention are well-known to those skilled in the art. The methods for assaying said biological markers have been described and used routinely in the laboratory for many years and there is thus no need to describe them in more detail herein.

According to one advantageous embodiment of the present invention, the expression of the candidate marker is normalised with respect to the expression of a control marker. A "control marker" according to the present invention is a marker whose expression is identical regardless of the cell type in question and the donor's age. In other words, the control marker is expressed to the same degree in children, and particularly in newborns, infants and/or children between 2 and 16 years, and adults.

According to one particular embodiment, when the candidate marker is a genetic marker or a protein marker, the control marker is a gene which is expressed in all cell types, regardless of the subject's age, or the protein product thereof. In one more particular embodiment, said control marker is a housekeeping gene which is expressed in all cell types and provides a basic function necessary for cell survival. A list of housekeeping genes may for example by found in Eisenberg et al. (Trends in Genetics 19: 362-365, 2003). A preferred housekeeping gene according to the invention is a gene selected from the group consisting of B2M, TFRC, YWHAZ, RPLO, 18S, GUSB, UBC, TBP, GAPDH, PPIA, POLR2A, ACTB, PGK1, HPRT1, IPO8 and HMBS.

It is clear for those skilled in the art that the invention offers the advantage of enabling easy isolation and characterisation of active agents, cosmetic starting materials and/or cosmetic formulations. In particular, the invention makes it possible to readily check the tolerance, skin penetration and efficacy of an active agent, a dermocosmetic composition or a cosmetic formulation. For example, it may be sought, in some cases, to check that these agents, these compositions or these formulations are well-tolerated and do not induce the expression of markers indicating stress, such as for example inflammation-related markers.

The invention thus also relates to a method for evaluating the tolerance of an active agent, a dermocosmetic composition or a cosmetic formulation, including the following steps:

a) obtaining at least one sample (A) of children's skin cells;

b) contacting an active agent, a dermocosmetic composition or a cosmetic formulation, with sample (A);

c) measuring the level of expression of at least one candidate biological marker characterising children's skin identified according to the method of the invention;

d) measuring the level of expression of said biological marker in a control sample;

e) calculating the ratio between the level of expression of step c) and the level of expression of step d), and f) determining whether said active agent, the dermocosmetic composition or the cosmetic formulation is well-tolerated by children's skin.

In a more preferred embodiment, the donor of sample (A) is more particularly a donor between 0 and 1 month of age, between 1 month and 2 years of age or between 2 and 16 years of age. In other words, according to this embodiment, the donor of sample (A) is chosen from the group consisting of newborns, between 0 and 1 month of age, infants, between 1 month and 2 years of age, and children between 2 and 16 years of age.

The control sample according to the invention is a sample which has not been in contact with the active agent, the dermocosmetic composition or the cosmetic formulation, which makes it possible to make a significant comparison between the level of expression of step c) and that of step d). For example, sample (A) which has not been treated with the active agent, the composition or the formulation may be used as a control. In this case, the level of expression of the biological marker according to the invention is measured in sample (A) before and after having been contacted with the active agent, the dermocosmetic composition or the cosmetic formulation.

The active agent is an active agent which is well-tolerated by children's skin if said active agent does not modulate the expression of the biological marker according to the invention. Likewise, the dermocosmetic composition or the cosmetic formulation are well-tolerated if the expression of the biological marker is not modulated by the addition thereof to sample (A). Said modulation may correspond, according to the case, and particularly according to the nature of the biological marker, to an increase or a decrease in the expression of said marker. In particular, the expression of inflammation markers is known to be increased when children's skin is attacked. On the other hand, the expression of these inflammation markers is not affected by well-tolerated active agents, compositions or formulations, as demonstrated by the experimental results of the present application. In one preferred embodiment, the biological marker of step c) is an inflammation marker. More preferably, the biological marker of step c) is IL1 or IL8.

The method according to the invention may further comprise a comparison of the cell viability in the sample treated with the agent, the composition or the formulation and in the control sample. In this case, the agent, the dermocosmetic composition or the cosmetic formulation is well-tolerated by children's skin if the cell viability of the sample is not affected by the presence of the active agent, the dermocosmetic composition or the cosmetic formulation. According to a further preferred embodiment, the method according to the invention thus includes an additional step for determining the cell viability in sample (A) treated with the active agent, the dermocosmetic composition or the cosmetic formulation, for determining the cell viability in the control sample and comparing both.

Numerous tests for determining the cell viability are available to those skilled in the art and are routinely used in cosmetology. Particularly mention is made of the MTT test, described for example in Mosman et al. (J Immunol Methods, 65(1-2): 55-63, 1983).

It may also be of interest to detect agents inducing increased expression of characteristic markers of a different age-group, such as, for example, genes and/or barrier proteins.

In a further aspect, the invention is thus suitable for isolating active agents having an effect on children's skin and, more particularly, on the skin of newborns, infants and/or children of 2 to 16 years of age. The identification of biological markers is suitable for identifying the active agents modulating the expression of these markers or not.

The invention thus also relates to a method for identifying an active agent for preparing a dermocosmetic composition for children, said method including the following steps:

a) obtaining at least one sample (A) of children's skin cells;

b) contacting a candidate active agent with sample (A);

c) measuring the level of expression of at least one biological marker characterising children's skin identified according to the method of the invention;

d) measuring the level of expression of said biological marker in a control sample;

e) calculating the ratio between the level of expression of step c) and the level of expression of step d), and f) determining whether said active agent is an active agent for preparing a dermocosmetic composition for children's skin.

In a more preferred embodiment, the donor of sample (A) is more particularly a donor between 0 and 1 month of age, between 1 month and 2 years of age or between 2 and 16 years of age. In other words, according to this embodiment, the donor of sample (A) is chosen from the group consisting of newborns, between 0 and 1 month of age, infants, between 1 month and 2 years of age, and children between 2 and 16 years of age.

The invention thus also relates to a method for identifying an active agent for preparing a dermocosmetic composition for children, said method including the following steps:

a) obtaining at least one sample (A) of skin cells, said sample being obtained from a donor, said donor being chosen from the group consisting of newborns, between 0 and 1 month of age, infants, between 1 month and 2 years of age, and children between 2 and 16 years of age;

b) contacting a candidate active agent with sample (A);

c) measuring the level of expression of at least one biological marker characterising children's skin identified according to the method of the invention;

d) measuring the level of expression of said biological marker in a control sample;

e) calculating the ratio between the level of expression of step c) and the level of expression of step d), and f) determining whether said active agent is an active agent for preparing a dermocosmetic composition for children's skin.

The control sample according to the invention is a sample which has not been in contact with the candidate active agent, which makes it possible to make a significant comparison between the level of expression of step c) and that of step d). For example, sample (A) which has not been treated with the candidate active agent may be used as a control. In this case, the level of expression of the biological marker according to the invention is measured in sample (A) before and after having been contacted with the candidate active agent.

The candidate active agent is an active agent for preparing a dermocosmetic composition for children's skin if said active agent is suitable for modulating the expression of the biological marker according to the invention. Said modulation may correspond, according to the case, and particularly according to the nature of the biological marker, to an increase or a decrease in the expression of said marker. In particular, it may be of interest to isolate active agents stimulating the expression of skin barrier markers or limiting inflammation markers.

In a further aspect, the invention is suitable for isolating starting material suitable for use in the development of formulations for children's skin and, more particularly, for the skin of newborns, infants and/or children of 2 to 16 years of age.

A formulation according to the invention is a preparation resulting from a mixture of various starting materials, in order to address a requirement expressed, generally, in terms of properties. The formulations according to the invention may be used in the field of cosmetics, pharmaceuticals, nutrition and/or nutraceuticals. They may be used in humans or animals, by topical or oral application.

The invention is thus suitable for identifying starting materials enhancing tolerance and skin penetration. The identification of biological markers according to the invention is suitable for identifying starting materials modulating the expression of these markers or not. The invention thus relates to a method for identifying a starting material suitable for use for preparing a cosmetic, pharmaceutical, nutritional and/or nutraceutical formulation for children, said method including the following steps:

a) obtaining at least one sample (A) of skin cells, said sample being obtained from a donor under 16 years of age;

b) contacting a candidate starting material with sample (A);

c) measuring the level of expression of at least one biological marker characterising children's skin identified according to the method of the invention;

d) measuring the level of expression of said biological marker in a control sample;

e) calculating the ratio between the level of expression of step c) and the level of expression of step d), and f) determining whether said candidate starting material is a starting material for preparing a cosmetic, pharmaceutical, nutritional and/or nutraceutical formulation for children.

According to one more preferred embodiment, the donor of sample (A) is more particularly a donor between 0 and 1 month of age, between 1 month and 2 years of age or between 2 and 16 years of age. In other words, according to this embodiment, the donor of sample (A) is chosen from the group consisting of newborns, between 0 and 1 month of age, infants, between 1 month and 2 years of age, and children between 2 and 16 years of age.

The invention thus also relates to a method for identifying a starting material suitable for use for preparing a cosmetic, pharmaceutical, nutritional and/or nutraceutical formulation for children, said method including the following steps:

a) obtaining at least one sample (A) of skin cells, said sample being obtained from a donor, said donor being chosen from the group consisting of newborns, between 0 and 1 month of age, infants, between 1 month and 2 years of age, and children between 2 and 16 years of age;

b) contacting a candidate starting material with sample (A);

c) measuring the level of expression of at least one biological marker characterising children's skin identified according to the method of the invention;

d) measuring the level of expression of said biological marker in a control sample;

e) calculating the ratio between the level of expression of step c) and the level of expression of step d), and f) determining whether said candidate starting material is a starting material for preparing a cosmetic, pharmaceutical, nutritional and/or nutraceutical formulation for children.

The control sample according to the invention is a sample which has not been in contact with the candidate starting material, which makes it possible to make a significant comparison between the level of expression of step c) and that of step d). For example, sample (A) which has not been treated with the candidate starting material may be used as a control. In this case, the level of expression of the biological marker according to the invention is measured in sample (A) before and after having been contacted with the candidate starting material.

It is clear that the invention is thus suitable, not only for isolating and characterising starting materials suitable for use in formulations, but further for testing formulations already prepared and for identifying those having optimal qualities in respect of tolerance, efficacy, toxicology and skin penetration for children's skin. Indeed, those skilled in the art will easily understand that it is not sufficient to measure the expression of one or a plurality of biological markers according to the invention to determine whether a formulation may be used on children's skin.

The invention thus relates to a method for identifying a cosmetic, pharmaceutical, nutritional and/or nutraceutical formulation for children, said method including the following steps:

a) obtaining at least one sample (A) of skin cells, said sample being obtained from a donor under 16 years of age;

b) contacting a candidate formulation with sample (A);

c) measuring the level of expression of at least one biological marker characterising children's skin identified according to the method of the invention;

d) measuring the level of expression of said biological marker in a control sample;

e) calculating the ratio between the level of expression of step c) and the level of expression of step d), and f) determining whether said candidate cosmetic formulation is a cosmetic, pharmaceutical, nutritional and/or nutraceutical formulation for children.

According to one more preferred embodiment, the donor of sample (A) is more particularly a donor between 0 and 1 month of age, between 1 month and 2 years of age or between 2 and 16 years of age. In other words, according to this embodiment, the donor of sample (A) is chosen from the group consisting of newborns, between 0 and 1 month of age, infants, between 1 month and 2 years of age, and children between 2 and 16 years of age.

The invention thus relates to a method for identifying a cosmetic, pharmaceutical, nutritional and/or nutraceutical formulation for children, said method including the following steps:

a) obtaining at least one sample (A) of skin cells, said sample being obtained from a donor, said donor being chosen from the group consisting of newborns, between 0 and 1 month of age, infants, between 1 month and 2 years of age, and children between 2 and 16 years of age;

b) contacting a candidate formulation with sample (A);

c) measuring the level of expression of at least one biological marker characterising children's skin identified according to the method of the invention;

d) measuring the level of expression of said biological marker in a control sample;

e) calculating the ratio between the level of expression of step c) and the level of expression of step d), and f) determining whether said candidate cosmetic formulation is a cosmetic, pharmaceutical, nutritional and/or nutraceutical formulation for children.

The control sample according to the invention is a sample which has not been in contact with the candidate formulation, which makes it possible to make a significant comparison between the level of expression of step c) and that of step d). For example, sample (A) which has not been treated with the candidate formulation may be used as a control. In this case, the level of expression of the biological marker according to the invention is measured in sample (A) before and after having been contacted with the candidate starting material.

According to a further aspect of the invention, the biological markers characterising children's skin are suitable for characterising skin disorders affecting children. More particularly, it is possible to characterise, using said biological markers according to the invention, skin diseases affecting newborns, infants and/or children between 2 and 16 years of age. The term "skin disorders" refers herein to any abnormal reactions liable to occur on a subject's skin. These conditions affect both the skin per se (i.e. the epidermis, dermis and/or hypodermis), and skin pores, the sweat and sebaceous glands appended thereto, hair or nails.

The skin disorders according to the invention give rise to lesions, corresponding to skin that is damaged or in poor condition. Damaged skin includes for example reactive sensitive skin, dry skin, skin damaged by the sun, radiation, cold, stress or pollution, by an allergy, urticaria, eczema and other forms of dermatitis such as atopic dermatitis, impetigo, irritative dermatitis, particularly irritative dermitis on the buttocks or nappy rash, contact dermatitis, seborrhoeic dermitis of the skin and scalp (cradle cap), psoriasis, Leiner-Moussous disease, or by wounds or burns. The term "skin disorder" thus includes disorders as diverse as dry patches, angioma (including tuberous, subcutaneous or plane), haemangioma, infantile acne, adolescent acne, ichthyosis (for example vulgaris, congenital, harlequin . . . ), etc. A skin disorder may also be caused or exacerbated by an external infection for example of parasitic, viral, bacterial or fungal origin. As such, skin disorders particularly include warts, prurigo strophulus, scabies, head lice infestation, or mycosis. The latter consists of parasitic infections caused by the proliferation of parasitic microscopic fungi on the body. Of the most frequent forms of mycosis, mention may be made of candidiasis and pitysporosis, caused by skin yeast proliferation.

According to this particular embodiment, the invention relates to a method for identifying at least one biological marker of a skin disorder affecting children, said method including the following steps:

a) obtaining at least one sample (A') of children's skin cells, said cells being obtained from a subject affected by said skin disorder;
    b) obtaining at least one control sample (B) of children's skin cells, said cells being obtained from a healthy subject;
    c) measuring the level of expression of at least one candidate biological marker in the sample of step a), said candidate biological marker being a biological marker characterising children's skin as identified according to the method of the invention described above;
    d) measuring the level of expression of said biological marker in the sample of step b),
    e) calculating the ratio between the level of expression of step a) and the level of expression of step b), and
    f) determining whether the candidate biological marker is a biological marker of a skin disorder affecting children.

According to one preferred embodiment, sample (A') is obtained from a donor who is more particularly a donor between 0 and 1 month of age, between 1 month and 2 years of age or between 2 and 16 years of age. In other words, according to this embodiment, the donor of sample (A) is chosen from the group consisting of newborns, between 0 and 1 month of age, infants, between 1 month and 2 years of age, and children between 2 and 16 years of age.

Preferentially, said candidate biological marker is a biological marker of a skin disorder if the level of expression thereof is different in healthy skin and in skin exhibiting the clinical characteristics of said skin disorder. More preferably, said marker characterises a skin disorder if said marker is expressed differentially in the subject affected by the skin disorder and the healthy subject. This gives rise to a ratio in step e) which is different to 1.

As those skilled in the art will easily realise, identifying specific markers of skin diseases in children (and particularly newborns, infants and/or children of 2 to 16 years of age) has the immediate advantage of being suitable for isolating active agents for treating said skin diseases.

The invention thus relates to a method for identifying an active agent for treating skin disorders in children, said method including the following steps:

a) obtaining at least one sample (A') of children's skin cells, said cells being obtained from a subject affected by said skin disorder;
    b) contacting a candidate active agent with the surface of said sample (A');
    c) measuring in sample (A') of step b) the level of expression of at least one candidate biological marker of said skin disorder affecting children identified according to the method of the invention described above;
    d) measuring the level of expression of said biological marker in at least one control sample,
    e) calculating the ratio between the level of expression of step c) and the level of expression of step d), and
    f) determining whether said candidate active agent is an active agent for treating skin disorders in children.

According to one preferred embodiment, sample (A') is obtained from a donor who is more particularly a donor between 0 and 1 month of age, between 1 month and 2 years of age or between 2 and 16 years of age. In other words, according to this embodiment, the donor of sample (A) is chosen from the group consisting of newborns, between 0 and 1 month of age, infants, between 1 month and 2 years of age, and children between 2 and 16 years of age.

Advantageously, an active agent for treating said skin disorder is capable of modulating the expression of said biological marker of said skin disorder. A candidate will thus be an active agent according to the invention if it gives rise to a different expression of said biological marker in the cells (A') untreated with said candidate and in the treated cells. In this case, the control of step d) will be advantageously an untreated sample (A'). More advantageously, said active agent is suitable for modulating the level of expression of said biological marker in the treated sample so that it is similar to that observed in a healthy sample. In this case, step d) will include the measurement of the level of expression of said biological marker in at least two control samples, one corresponding to an untreated sample (A') and the other to a healthy sample (B). If the candidate marker is an active agent for treating skin disorders, it should then be observed that the ratio between the levels of expression of treated (A') and untreated (A') is different to 1, whereas that between the levels of expression of (A') and (B) is close to 1.

The invention will be described more specifically using the examples below.

EXAMPLES

Example 1

In order to identify the biological markers characterising children's skin, the present inventors conducted a genomic analysis study according to the children's age.

Materials and Methods

Skin samples were taken (foreskin removal or breast plasty, according to the donor's sex) on donors of 1 month, 3 months, 3 years, 6 years and 11 years of age, and on adults.

Reconstructed skin models were generated using these samples. Reconstructed epidermises were thus produced with the various donors selected using the technique by Poumay et al. (Arch Dermatol Res, 296(5): 203-211, 2004). After two days of submerged culture, the reconstructed epidermises were cultured at the air/liquid interface for 5 or 9 days. For the duration of the culture, the medium was replenished every 2 to 3 days.

At the end of incubation, the epidermises were rinsed and half frozen and half fixed in a formaldehyde solution. Cross-sections were produced in the fixed tissues with a microtome, in order to check the structure of the epidermises.

In parallel with these reconstructed epidermises, mono-layer cultures of keratinocytes from the various samples were produced. The various keratinocytes were inoculated in culture medium in a 12-well plate. After 48 hours of incubation (day of air liquid passage for reconstructed epidermises), the cell sheets were lysed with TRIPURE ISOLATION REAGENT® (Roche Applied Science) and frozen at −80° C.

At the end of incubation, the epidermises or cell sheets were lysed with TRIPURE ISOLATION REAGENT® and the total RNA was extracted according to the protocol recommended by the supplier. The quantity and quality of the RNA were evaluated using the Bioanalyzer (Agilent Technologies). Each RNA sample was aliquoted, a portion of the sample being used for microchip hybridisation, the remainder being frozen before being used for a quantitative RT-PCR experiment.

The RNA was amplified and labelled using the GeneChip 3'IVT Express Kit (Affymetrix) according to the protocol recommended by the supplier. They were then hybridised on the AFFYMETRIX® chip in the AFFYMETRIX® GENEATLAS™ fluidics station hybridisation station for 16 hours at 45° C. This step was performed using the "GENEATLAS™ hybridization, wash and stain kit for 3' IVT arrays" kit (AFFYMETRIX®). The U219 chip was analysed using the GENEATLAS™ Imaging station scanner.

The data obtained by means of chip hybridisation were processed and normalised using the software supplied by Affymetrix (AFFYMETRIX® GCOS, AFFYMETRIX® Expression Console).

The results obtained by means of chip hybridisation were confirmed by means of RT quantitative PCR (RT-qPCR). For this, the RNA prepared is first retro-transcribed to cDNA in the presence of oligo(dT) using Superscript II enzyme (Gibco).

Results

The histological analysis demonstrated that all the reconstructed epidermises had the expected morphology on D5 and D12, regardless of the donor, suitable for validating the genic analysis results. In particular, the basal layer, the spinous layer, the granular layer and the corneal layer were found in each epidermis. Furthermore, as expected, the thickness thereof was greater on D12 than on D5.

The genomic analysis was suitable for identifying a plurality of markers wherein the expression varies according to the donor's age. These results were confirmed by means of RT quantitative PCR. The markers were then categorised by biological function, using Ariadne GENOMICS PATHWAY STUDIO®.

Figure 1B:
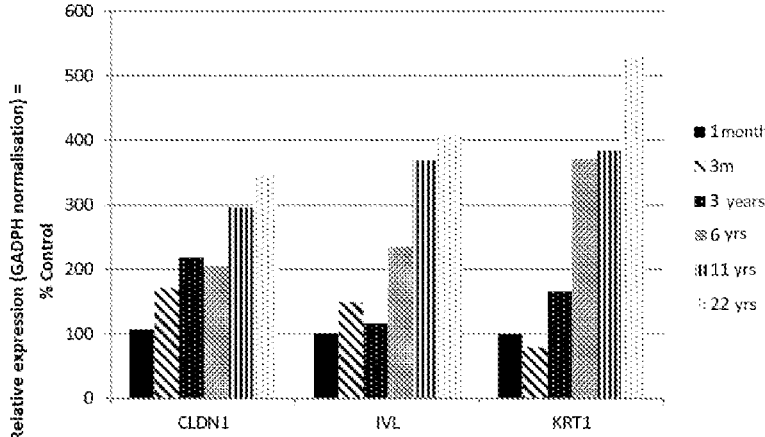

It was thus possible to identify a group of skin barrier genes, including the genes CLDN1, IVL, KRT1. The expression of these epidermal barrier function genes increases with age in reconstructed epidermises (FIG. 1A); on the other hand, these genes are less expressed in the youngest subjects. These results were confirmed by means of RT quantitative PCR analysis in the keratinocytes (FIG. 1B). The results obtained with the reconstructed epidermises and the keratinocytes are similar in terms of expression profile, which validates the approach adopted. It is furthermore of interest to note that these results, similar to those of Fluhr et al. (Exp Dermatol., 19(6): 483-492, 2010), illustrate the maturation with age of the skin barrier function.

Figure 2A:
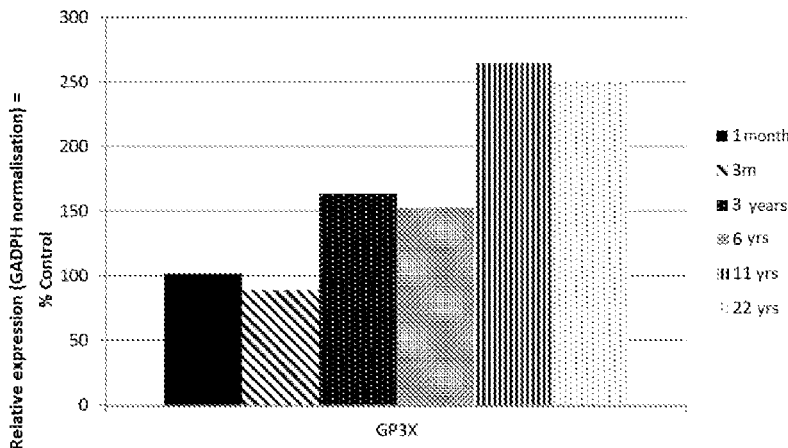
Figure 2B:
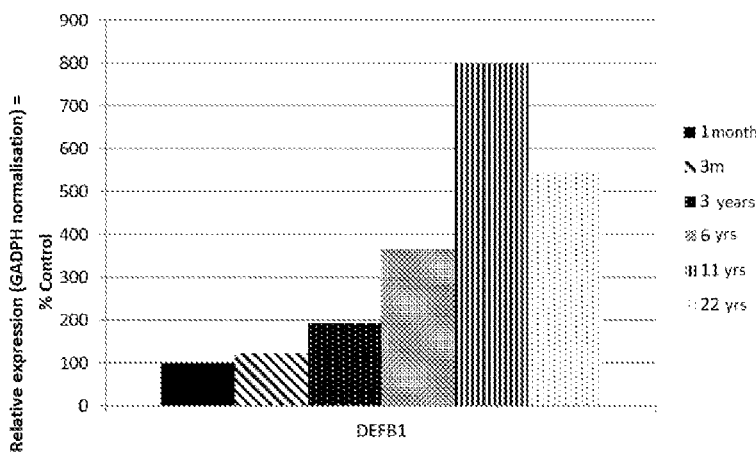

Similarly, the expression of stress response (GPX3) and innate defence (DEFB1) genes increases with age (FIGS. 2A and 2B, respectively).

On the other hand, the expression of the MGST1 gene declines with age (FIG. 3). This gene is expressed significantly in children of 1 and 3 months, but the transcription thereof subsequently declines by a factor at least equal to 5.

Finally, the expression of the stem cell genes, FN1, NOTCH1, NID1, KRT19, ITGBP1, ITGA6 and ITGB4, is high after birth and declines with age (FIG. 4).

Example 2

The tolerance of products based on avocado C7 sugars (avocado perseose, see for example WO 2005/115421, WO 2008/025847 and WO 2011/073281) were evaluated on reconstructed epidermises from donors of 1 month of age.

Materials and Methods

Epidermises were reconstructed as specified in example 1 with keratinocytes from donors of 1 month of age. The products, a cleansing cream and a moisturising lotion both containing avocado perseose, were applied on these reconstructed epidermises for 16 hours. A control was produced by applying 0.4% SDS on control reconstructed epidermis samples.

IL-8 protein was assayed in the culture supernatant using an Elisa test. The cell viability was evaluated using the MTT test. Finally, a histological analysis was conducted on tissues included in paraffin by means of haematoxylin and eosin staining.

Results

The result reported on table 1 demonstrate that cell viability is not affected by applying cleansing cream or moisturising lotion containing avocado perseose. In comparison, the cell viability of the epidermis treated with SDS is very significantly reduced, since only 2% of the cell are still alive after treatment.

Moreover, the thickness of the layers of live cells is maintained at a similar level to that of the control in the samples treated with products containing avocado perseose. In comparison, the histological analysis demonstrates that the layers of live cells in the epidermis treated with SDS correspond merely to 50-60% of the thickness observed in the control (FIG. 5).

The cell biology results are confirmed by the IL-8 cytokine activation analysis in response to the various treatments. While SDS induces a significant increase in the expression of this protein, no effect is observed when the reconstructed epidermises are treated with cleansing cream or moisturising lotion containing avocado perseose.

All these results thus demonstrate that both products containing avocado perseose are not toxic and are well-tolerated.

TABLE 1

|  | Control | + 0.4% SDS | + Cleansing cream | + Moisturising lotion |
|---|---|---|---|---|
| Viability | 100% | 2% | 84% | 93% |
| IL8 inflammatory molecule | 100% | 602% | 99% | 89% |
| Thickness of live layers | 100% | 58% | 88% | 87% |

The invention claimed is:

1. A method for evaluating the tolerance, by children's skin, of a composition comprising mannoheptulose and perseitol comprising the following steps:
   a) measuring the level of expression or the activity of a combination of candidate biological markers in at least one reconstructed skin culture (A), said culture being obtained from a donor under 16 years of age, wherein said combination of candidate biological markers of children's skin is the combination of genes, proteins, hormones or enzymes consisting of:
   IGFL3 (IGF-like family member 3);
   GP3X (glutathione peroxidase 3);
   MGST1 (microsomal glutathione S-transferase 1);
   DEFB1 (defensin beta1);
   DEFB4 (defensin beta4);
   CDKN1 (cyclin-dependent kinase inhibitor);
   BARX2 (BARx Homeobox 2);
   SCEL (sciellin);
   CLDN1 (claudin 1);
   IVL (involucrin);
   KRT1 (keratin 1);
   CADM1 (cell adhesion molecule 1);
   FN1 (fibronectin 1);
   NID1 (nidogen 1);
   NOTCH1 (Notch homolog 1, translocation-associated);
   KRT19 (keratin 19);
   ITGB1BP1 (integrin beta1 binding protein);
   ITGA6 (integrin alpha6); and
   ITGB4 (integrin beta4);
   b) measuring the level of expression or the activity of said combination of candidate biological markers in at least one control sample (B) of skin cells, wherein the control sample (B) is obtained from an adult,
   c) determining that the combination of candidate markers is a combination of biological markers of children's skin, wherein the level of expression or the activity of step b) is different from the level of expression or the activity of step a), wherein said combination of candidate biological markers is a combination of biological markers of children's skin;
   d) contacting a composition comprising mannoheptulose and perseitol, with the reconstructed skin culture (A);

e) measuring the level of expression of interleukin 8 (IL8), and measuring the level of expression or the activity of the combination of biological markers of children's skin of step c) in the reconstructed skin culture (A) after step d); and
   f) measuring the level of expression of interleukin 8 (IL8), and measuring the level of expression or the activity of the combination of biological markers of children's skin of step c) in a control sample; and
   g) determining the tolerance of the composition, by children's skin based on the levels of expression or the activity measured in steps e) and f), and
   h) preparing a cosmetic, pharmaceutical, nutritional and/or nutraceutical formulation for children if, and only if, the composition does not significantly modulate the level of expression of interleukin 8 (IL8) and the composition does not significantly modulate the level of expression or the activity of the combination of markers of children's skin.

2. The method according to claim 1, wherein culture (A) is obtained from a donor selected from the group consisting of newborns, between 0 and 1 month of age, infants, between 1 month and 2 years of age, and children between 2 and 16 years of age.

3. The method according to claim any of claim 1 or 2, wherein in step a) the level of expression or the activity of candidate biological marker is measured in at least two reconstructed skin cultures.

4. The method according to claim 3, wherein said two cultures belong to two different age-groups.

5. The method according to claim 1, wherein cells of said culture are obtained from an explant of skin tissue or stem cells differentiated to skin cells.

6. The method according to claim 1, wherein the culture comprises at least fibroblasts or keratinocytes.

7. The method according to claim 1, wherein the reconstructed skin is selected from the group consisting of dermis models, epidermis models, hypodermis models, skin models including a dermis and an epidermis, and skin models including a dermis, an epidermis and a hypodermis.

8. A method for evaluating the tolerance, by children's skin, of a composition comprising mannoheptulose and perseitol comprising the following steps: a) measuring the level of expression or the activity of a combination of candidate biological markers in at least two reconstructed skin cultures (A) and (A'); said culture (A) being obtained from a newborn donor, between 0 and 1 month of age, and said culture (A') being obtained from an infant donor, between 1 month and 2 years of age, wherein said combination of candidate biological markers of children's skin is the combination of genes, proteins, hormones or enzymes consisting of:
   IGFL3 (IGF-like family member 3); GP3X (glutathione peroxidase 3); MGST1 (microsomal glutathione S-transferase 1); DEFB1 (defensin beta 1); DEFB4 (defensin beta4); CDKN1 (cyclin-dependent kinase inhibitor); BARX2 (BARx Homeobox 2); SCEL (sciellin); CLDN1 (claudin 1); IVL (involucrin); KRT1 (keratin 1); CADMI (cell adhesion molecule 1); FN1 (fibronectin 1); NID1 (nidogen 1); NOTCHI (Notch homolog 1, translocation-associated); KRT19 (keratin 19); ITGB1BP1 (integrin beta1 binding protein); ITGA6 (integrin alpha6); andITGB4 (integrin beta4);
   b) measuring the level of expression or the activity of said combination of candidate biological markers in at least one control sample (B) of skin cells, wherein the control sample (B) is obtained from an adult, c) determining that the combination of candidate markers is a combination of biological markers of children's skin, wherein the level of expression or the activity of step b) is different from the level of expression or the activity of step a), wherein said combination of candidate biological markers is a combination of biological markers of children's skin;

d) contacting a composition comprising mannoheptulose and perseitol, with the reconstructed skin culture (A) and (A');

e) measuring the level of expression of interleukin 8 (IL8), and measuring the level of expression or the activity of the combination of the biological markers of children's skin of step c) in the reconstructed skin culture (A) and (A') after step d); and f) measuring the level of expression of interleukin 8 (IL8), and measuring the level of expression or the activity of the combination of the biological markers of children's skin of step c) in a control sample;

g) determining the tolerance of the composition, by children's skin based on the levels of expression or the activity measured in steps e) and f), and h) preparing a cosmetic, pharmaceutical, nutritional and/ or nutraceutical formulation for children if, and only if, the composition does not significantly modulate the level of expression of interleukin 8 (IL8) and the composition does not significantly modulate the level of expression or the activity of the combination of markers of children's skin.

9. The method according to claim 1, wherein the control sample of step f) is the reconstructed skin culture (A) which has not been contacted with the composition.

10. The method according to claim 8, wherein the control sample of step f) is the reconstructed skin culture (A) which has not been contacted with the composition.

11. The method according to claim 1, wherein the level of expression of said gene is determined using a method selected from the group consisting of Northern Blot, Southern Blot, PCR, RT-PCR, RT quantitative PCR, SAGE, nucleic acid chips, oligonucleotide chips and mRNA chips, tissue chips and RNA-Seq; and wherein the level of expression of said protein is determined using a method selected from the group consisting of immunohistology, immunoprecipitation, Western Blot, Dot Blot, ELISA, ELISPOT, protein chips, antibody chips, tissue chips coupled with immunohistochemistry, FRET techniques, BRET techniques, microscopy methods, histochemistry methods, an electrochemical method, atomic force microscopy, radiofrequency methods, surface plasmon resonance, ellipsometry, resonant mirror biosensor flow cytometry, radioisotopic imaging, magnetic resonance imaging, polyacrylamide gel electrophoresis (SDS-PAGE), HPLC-Mass spectrophotometry, and liquid chromatography-mass spectrophotometry/mass spectrometry (LC-MS/MS).

12. The method according to claim 8, wherein the level of expression of said gene is determined using a method selected from the group consisting of Northern Blot, Southern Blot, PCR, RT-PCR, RT quantitative PCR, SAGE, nucleic acid chips, oligonucleotide chips and mRNA chips, tissue chips and RNA-Seq; and wherein the level of expression of said protein is determined using a method selected from the group consisting of immunohistology, immunoprecipitation, Western Blot, Dot Blot, ELISA, ELISPOT, protein chips, antibody chips, tissue chips coupled with immunohistochemistry, FRET techniques, BRET techniques, microscopy methods, histochemistry methods, an electrochemical method, atomic force microscopy, radiofrequency methods, surface plasmon resonance, ellipsometry, resonant mirror biosensor flow cytometry, radioisotopic imaging, magnetic resonance imaging, polyacrylamide gel electrophoresis (SDS-PAGE), HPLC-Mass spectrophotometry, and liquid chromatography-mass spectrophotometry/mass spectrometry (LC-MS/MS).

* * * * *